United States Patent
Obata et al.

(10) Patent No.: US 7,252,633 B2
(45) Date of Patent: Aug. 7, 2007

(54) REMOTE CONTROLLABLE ENDOSCOPE SYSTEM

(75) Inventors: Mitsuo Obata, Tokyo (JP); Saichi Sato, Sagamihara (JP)

(73) Assignee: Olympus Corporation (JP)

( * ) Notice: Subject to any disclaimer, the term of this patent is extended or adjusted under 35 U.S.C. 154(b) by 366 days.

(21) Appl. No.: 10/688,622

(22) Filed: Oct. 17, 2003

(65) Prior Publication Data

US 2004/0225185 A1 Nov. 11, 2004

(30) Foreign Application Priority Data

Oct. 18, 2002 (JP) ............................. 2002-304939
Oct. 18, 2002 (JP) ............................. 2002-304940
Apr. 11, 2003 (JP) ............................. 2003-107859

(51) Int. Cl.
*A61B 1/045* (2006.01)
(52) U.S. Cl. .................... 600/118; 600/109; 600/101
(58) Field of Classification Search ............... 600/118, 600/101, 109, 407; 348/65, 74
See application file for complete search history.

(56) References Cited

U.S. PATENT DOCUMENTS 5,217,003 A * 6/1993 Wilk ........................ 600/109

| | | | |
|---|---|---|---|
| 5,609,560 A * | 3/1997 | Ichikawa et al. ........... 600/101 |
| 5,622,528 A * | 4/1997 | Hamano et al. ............. 600/118 |
| 5,724,355 A * | 3/1998 | Bruno et al. ................. 370/401 |
| 6,106,457 A * | 8/2000 | Perkins et al. .............. 600/175 |
| 6,393,431 B1 | 5/2002 | Salvati et al. |
| 6,397,286 B1 * | 5/2002 | Chatenever et al. ........ 710/302 |
| 6,490,490 B1 * | 12/2002 | Uchikubo et al. ............ 700/65 |
| 6,581,117 B1 * | 6/2003 | Klein et al. ................. 710/110 |
| 6,602,185 B1 * | 8/2003 | Uchikubo .................... 600/118 |
| 7,006,895 B2 * | 2/2006 | Green ......................... 700/245 |
| 2003/0004397 A1 * | 1/2003 | Kameya et al. ............. 600/101 |
| 2003/0097042 A1 * | 5/2003 | Eino ............................ 600/118 |
| 2005/0075556 A1 * | 4/2005 | Pan ............................. 600/407 |

FOREIGN PATENT DOCUMENTS

| JP | 11-211997 | 8/1999 |
|---|---|---|
| JP | 2000-245738 | 9/2000 |
| JP | 2003-135372 | 5/2003 |

* cited by examiner

*Primary Examiner*—John P. Leubecker
(74) *Attorney, Agent, or Firm*—Ostrolenk, Faber, Gerb & Soffen, LLP

(57) ABSTRACT

An endoscope control system comprises a network server device which is provided with an interface for executing an external application software and stores a graphical user interface (GUI) which is a display information which is written in at least a server language and external application software, and a network interface (network I/F). By doing this, it is possible to control remotely the endoscope device without connecting the endoscope device and the control section.

11 Claims, 32 Drawing Sheets

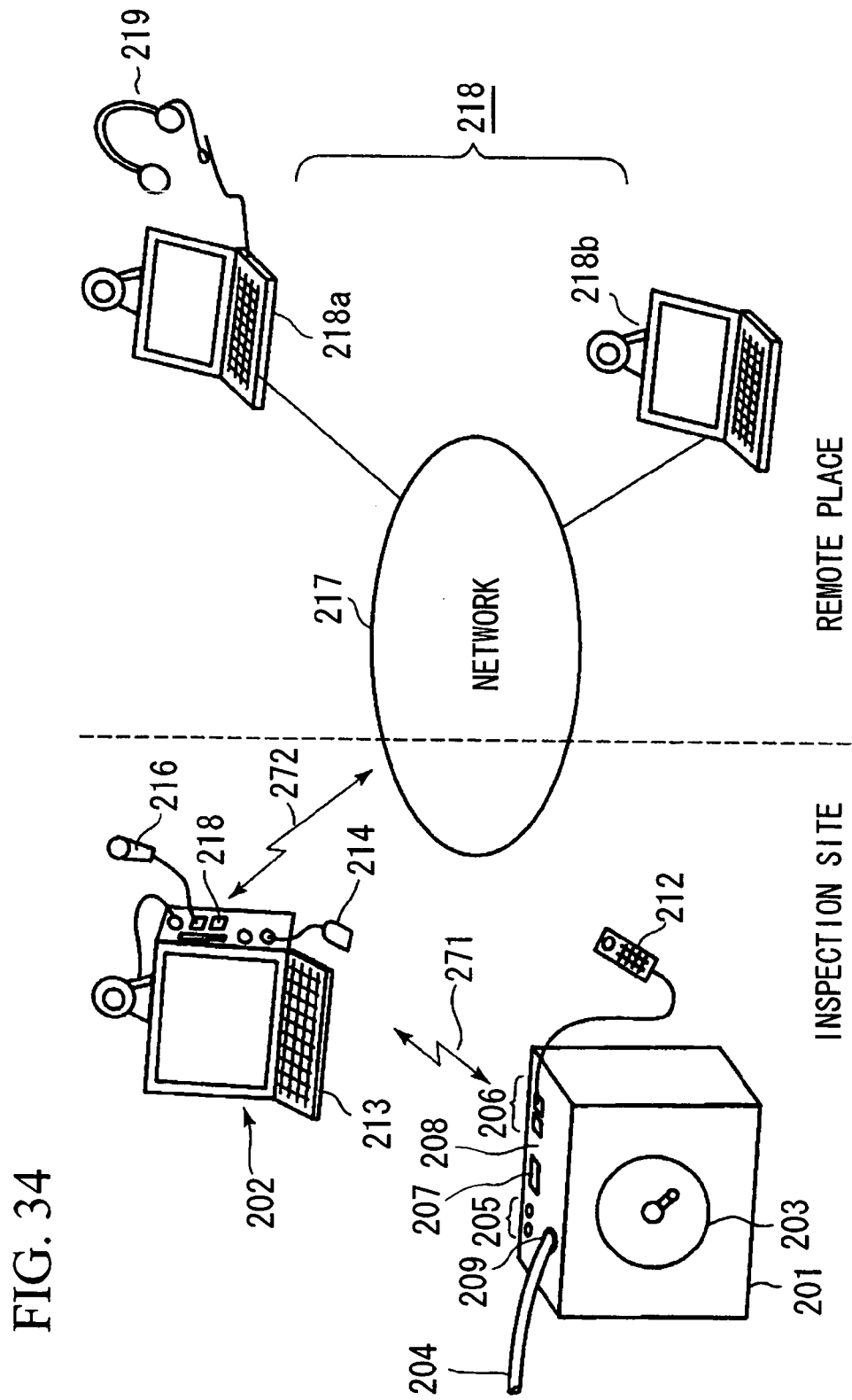

REMOTE CONTROLLABLE ENDOSCOPE SYSTEM

The present application is based on patent applications No. 2002-304939 filed Oct. 8, 2002 in Japan, 2002-304940 filed Oct. 18, 2002 in Japan, and No. 2003-107859 filed Apr. 11, 2003 in Japan, the content of which are incorporated herein by reference.

BACKGROUND OF THE INVENTION

1. Field of the Invention

The present invention relates to a remote controllable endoscope control system which can observe and operate an endoscope system which is used in an industrial use via a communication line which includes a network by a remote external terminal.

2. Description of Related Art

In general, an endoscope system is used for a non-destruction examination in an industrial use. If a sample object to be observed (an area as an object for the examination) is large or a sample object o be observed is already installed, disassembled endoscope system are brought to a site near the sample object so as to be assembled by examiner etc. Techniques for such an endoscope system are proposed in Japanese Unexamined Patent Application, First Publications No. 2003-135372, 2000-245738, and Hei 11-211997.

SUMMARY OF THE INVENTION

An endoscope control system according to the present invention comprises a network server device which is provided with an interface for executing an external application software and stores a graphical user interface (GUI) which is a display information which is written in at least a server language and external application software, and a network interface (network I/F).

In the present invention, it is preferable that the external application software should be formed by a computer program.

In the present invention, it is preferable that the external application software should be formed by a script.

Also, in the present invention, it is preferable that the interface should be formed by a common gateway interface (CGI).

Also, in the present invention, it is preferable that the interface should be formed by an active server pages (ASP).

An endoscope control system according to the present invention comprises an endoscope device which is provided with insertion section for taking an image for an inner section of a sample object for obtaining an endoscope image, a control section which is connected to the endoscope device via a cable and has a server for performing a network communication so as to transmit and receive the endoscope image by an electric signal or an optical signal and control a driving operation for the endoscope device, a communication network structure which is connectable to the control section, and at least an external terminal which has a function for operating the endoscope device while observing the endoscope image via the communication network such that the endoscope device is controlled remotely by the external terminal when the external terminal and the control section are connected by the communication network.

Also, the endoscope control system according to the present invention further comprises a control section which is provided with a first image and a voice capture, at least an external terminal which is provided with a server which is connectable to the communication network structure and a function for operating the endoscope device while observing the endoscope image, such that each external terminal has a second image and a voice capture, a mutual communication is performed between the first image with the voice capture and the second image with the voice capture in addition to the endoscope image when the external terminals and the control section are connected via the communication network.

Also, in the present invention, it is preferable that the server should convert the instruction from the external terminal and/or the control section for controlling the driving operation for the endoscope to a signal for controlling the driving operation for the endoscope by using the script.

Also, an endoscope control system of the present invention comprises an endoscope device which is provided with an insertion section which takes an image for an inner section of a sample object so as to obtain an endoscope image so as to perform a communication for an information which includes the endoscope image by connecting to a communication network, a remote control device which has a function for displaying image which can perform be connect to the network and to the endoscope device mutually via the network so as to be controlled remotely while observing an image which is outputted from the endoscope device and an information which relates to the outputted image, at least an external terminal which is connected to the endoscope via the network and has a function for operating the endoscope device while observing the endoscope image such that the operation for taking an image by the endoscope is controlled remotely when the remote control device or the external terminal is connected to the endoscope via the communication network.

Also, in the present invention, it is preferable that, in an endoscope control system, the remote control device and the external terminal should have a microphone and speaker and/or a camera respectively, and the remote control device and the external terminal perform a mutual communication via the network such that circumstance condition around the remote control device and the external terminal are exchanged by using a voice and image.

Also, it is preferable that, in an endoscope control system according to the present invention, an image display section and an operation switch section are disposed separately in the remote control device which has a function for displaying image such that the operation switch section is connected to the endoscope device via a wireless communication so as to control the driving operation by transmitting an operation signal.

Also, in the present invention, it is preferable that the connection between the control section and the external terminal should be controlled exclusively by an identification number (ID) or a password such that the driving operation for the endoscope should be controlled only by the external terminal which is allowed by the control section.

Also, an endoscope control system according to the present invention comprises an endoscope device which is provided with insertion section for taking an image for an inner section of a sample object for obtaining an endoscope image, a control section which is connected to the endoscope device via a wireless communication and has a server for performing a network communication so as to transmit and receive the endoscope image by an electric signal or an optical signal and control a driving operation for the endoscope device, a communication network structure which is connectable to the control section; and at least an external terminal which has a function for operating the endoscope device while observing the endoscope image via the communication network such that the endoscope device is controlled remotely by the external terminal when the external terminal and the control section are connected by the communication network.

BRIEF DESCRIPTION OF THE DRAWINGS

FIG. 34 is a view for a general structure of a remote controllable endoscope control system according to a seventh embodiment of the present invention.

DETAILED DESCRIPTION OF THE INVENTION

Embodiments of the present invention are explained in detail with reference to drawings as follows.

Figure 1:
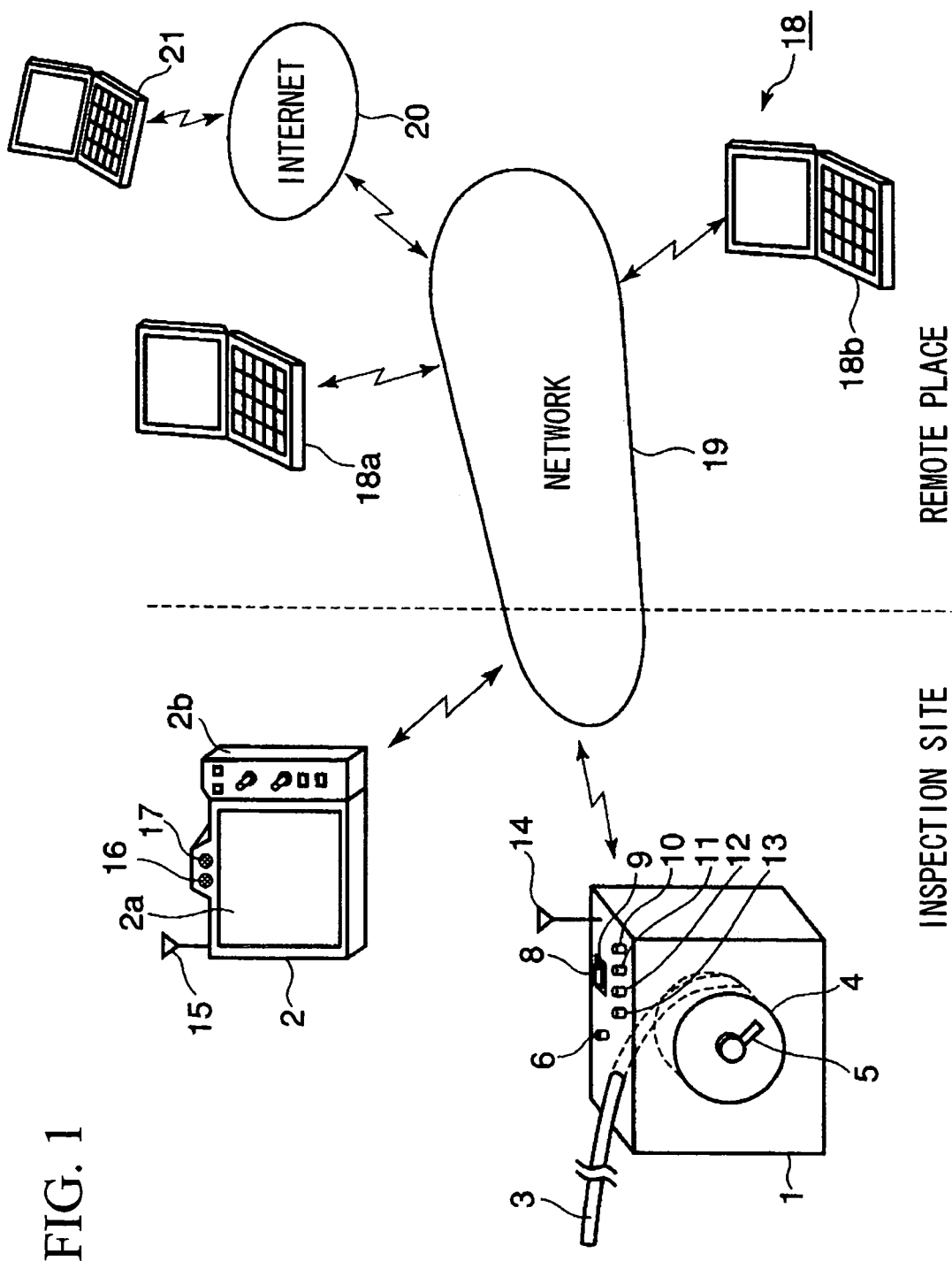
FIG. 1 is a view for a general structure of a remote controllable endoscope control system according to a first embodiment of the present invention.

FIG. 1 is a view for a general structure of a remote controllable endoscope control system according to a first embodiment of the present invention. In embodiments below in the endoscope control system according to the present invention, explanations are made for a case in which the above explained endoscope device main body and a peripheral sections are contained unitarily in a frame so as to be movable. However, the present invention is not limited to such a structure. A structure in which the endoscope device and peripheral sections are separable can be used for a communication system according to the present invention.

The endoscope system comprises an endoscope device 1 which has a communication function for an image etc. by connecting to a network 19 such as a LAN (local area network) via a wireless communication and a remote control device 2 which has an image display function which can be connected to a network 19 via a wireless communication so as to control a driving operation for the endoscope device 1 and communicate an information which includes an image (endoscope image). In the wireless communication, an identification number (ID) and a password are referred such that at least a main remote control device 2 which is verified as the endoscope device 1 and the external terminals 18, 21 may be connected. By doing this, it is possible to avoid an erroneous connection by other non-verified apparatuses.

An insertion section 3 which is wound around a rotative drum 4 in the endoscope 1 is contained in a main body of the endoscope device 1. A connecting section 6 for remote control device which is used for connecting to other remote control devices (a cable main remote control device) via a cable in case in which it is not possible to use a wireless communication, a PC card slot 9 to which a PC card 8 is disposed for recording an information which includes an image, an external voice input section 10 into which a microphone (not shown in the drawing), an external voice outputting section 11 which is used for connecting to an external speaker (not shown in the drawing), an external image outputting section 13 for outputting an image signal to a display section (not shown in the drawing) such as a monitor, and an antenna 14 for performing a wireless communication are disposed on an upper surface of a main body of the device. Also, a moving caster and a draw bar (not shown in the drawing) are disposed on a bottom part of the endoscope device 1 for a convenience for a transportation.

The communication by the endoscope device 1 is performed by a WWW (Web) server such that an information which includes an image which is described by a server language such as an HTML should be transmitted by using a wireless communication interface section (communication I/F section). For such a Web server, it is possible to name an IIS (Internet Information Server, a trademark for product is registered by Microsoft). Also, for an example of an Apatche Web browser, it is possible to name an IE (Internet Explorer, a trademark for product is registered by Microsoft). For example, it is possible to name an HTML and XML for a server language. For a wireless communication interface section, an IEEE802.11b or an IEEE 802.11a are known. Also, an HTTP is known for a communication protocol.

Here, an HTML is explained which is used in a server language in the present invention. The HTML file which is described by HTML is stored in a hard disk (an HD 68 in FIG. 4).

The Web server which is disposed in the endoscope device 1 transmits data which relate to the HTML and corresponding data such as a graphic data for operation buttons which are displayed in a display, a live image which is captured by the endoscope device 1, and images which are stored in the endoscope 1 to the main remote control device 2 and the external terminal 18 according to a request from the main remote control device 2 and the external terminal 18 (21) as a client.

The Web browser which are disposed in the main remote control device 2 and the external terminal 18 downloads the HTML file from the endoscope device 1 so as to display an hypertext which is written in the HTML on a display graphically. Information which relate to images such as an URL in which data and time are stored are displayed in the above display together with buttons shown in FIG. 20 etc., a list for the sample object, and operation devices such as a link to the URL.

Also, the Web server executes an external application software via an interface such as a CGI (Common Gateway Interface) and an ASP(Active Server Pages) so as to return the result of the executed software to the Web browser if a link which is requested by a Web browser for the main remote control device 2 and the external terminal 18 (21) is designated to the external application software. The interface for executing the external application software depends on the external application software at the link such that the interface should be selected by the Web server appropriately. Also, the external application software is written in a C-language or a Perl-language.

Figure 2:
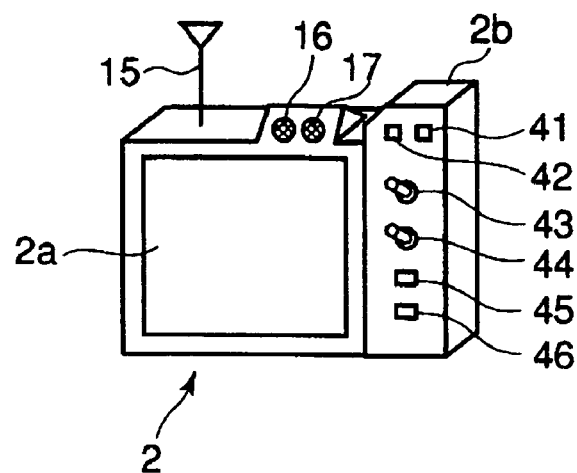
FIG. 2 is an external view for a main remote control section according to the first embodiment.

FIG. 2 is an external view for the main remote control device 2.

The main remote control device 2 is formed by an image display section 2a which is formed by a liquid display element (LCD) and a switch section 2b to which various switches are disposed. An antenna 15 for performing a wireless communication with the network 19, a microphone 16 which collects a voice etc. of a person who conducts a test and manipulates the main remote control device 2, and a speaker 17 for emitting the received voice are disposed on an upper surface of the image display section 2a.

Also, the switch section 2b is provided with a zoom button 41 for enlarging an image for sections of the sample object which is captured by an image (endoscope image) capturing element (CCD) which is disposed on a tip of the insertion section 3 in the endoscope device 1, an electrical angle joystick 43 for bending the tip of the insertion section 3 for obtaining a desirable endoscope image, an instruction switch 44 which is movable in four directions for selecting and confirming the instruction and items by a menu display etc., and a live button 46 which can switch a live image for the endoscope image which is currently captured by the CCD and a freeze image (a temporary paused image of the live image).

The main remote control section 2 is provided with WWW browser. The main remote control section 2 can display the image (which includes the endoscope image and a real-time image) which is regularly transmitted from the endoscope 1. Also, the main remote control device can display informations which relate to the image. Also, the main remote control device 2 is provided with a graphical user interface(GUI) such that the main remote control device 2 can control the driving operation for the endoscope device 1 remotely by using the GUI according to the image from the main body of the endoscope and the corresponding information.

More specifically, the GUI can be accessed by the endoscope 1 and the external terminal 18 and controlled remotely by sending an instruction to the image for the user interface which is displayed on the display 2a of the main remote control device. Such a GUI is explained with reference to "B+" button which is indicated by reference numeral 163 in FIG. 23. The "B+" button serves for adjusting a parameter such as "Brightness" which indicates the brightness in the endoscope image upwardly. The link for the "B+" button is stored in a Web server in the endoscope device 1 as an external application software. When the "B+" button is pressed in a display 2a in the main remote control device 2, the Web server executes the external application software for the "B+" via the CGI interface. The B+ application software instructs such that the endoscope control section 66 should increase the Brightness of the CCU 63. The endoscope control section 66 transmits an UP command for the Brightness to the CCU 63. When the CCU 63 receives the above command, the CCU 63 adjusts the brightness in the image signal and outputs the adjusted image signal. Here, the above command is realized by a serial communication such as an RS-232.

Also, "T" button serves for enlarging (zoom up) a size of the endoscope image. The link of the "T" button is stored in the Web server in the endoscope device 1 as an external application software. The system control section (CPU 102 shown in FIG. 6) in the main remote control device 2 transmits such a click operation from the network I/F section (a communication I/F section 111 shown in FIG. 6) to the endoscope device 1. The Web server which receives a request from a client such as a main remote control device 2 in the endoscope device 1 executes an image enlargement external application software as a link via the CGI interface. The image enlargement application software instructs to the endoscope control section 66 such that the endoscope control section 66 should enlarge the endoscope image which is outputted from the CCU 63. The endoscope control section 66 transmits an image enlargement command to the CCU 63. When The CCU63 receives the above command, the CCU 63 enlarges a part of the image signal so as to output an image signal as a portion of a display.

Also, when an URL is inputted on an address bar, it is possible to download a desirable HTML so as to be displayed on the browser.

Also, an area for displaying the image which is transmitted from the endoscope device 1 is disposed in the HTML file such that the image which is received by the main remote control device 2 is displayed in the display area. More specifically, if a still image is received, such a still image which is archived in a still image archive section (a still image archive section 109 shown in FIG. 6) is displayed in a desirable area which is described in the HTML file. On the other hand, the live image (a motion image) is also archived in a motion image archive section (a motion image archive section 110 shown in FIG. 6) so as to be displayed in a desirable area which is described in the HTML file. Such an archive operation is performed on real-time; thus, the main remote control device 2 can display an image which is captured by the endoscope device 1 under a real-time condition.

If an instruction for recording such images is issued and a recording device designates a PC card for the endoscope device 1 in a menu which is not shown in the drawing, the image which is compressed by the endoscope device 1 is recorded in the PC card 8. On the other hand, if the recording device designates the main remote control device 2 and the external terminal 18 in a menu which is not shown in the drawing, the compressed image which is received is stored in the storage device in each device while the compressed image is archived and displayed. For example, for such a storage device, it is possible to name a hard disk drive unit and a PC card.

Furthermore, it is possible to connect the network 19 to a plurality of external terminals 18 (18a, 18b) which are formed by a personal computer, etc. These external terminals 18 can be connected to the endoscope device 1 via the network 19 such that these external terminals 18 are provided with the WWW browser. These external terminals 18 can receive and display the information which is transmitted from the endoscope device 1 such as an endoscope image (real-time image) which is captured by the endoscope (insertion section 3), an image information which relates to an endoscope image, and a recording image which is read out from the endoscope device 1. Also, these external terminals are provided with a GUI such that these external terminals can perform a driving operation for the endoscope device 1 remotely according to the image information. The main remote control device 2 and the external terminal 18 in the present embodiment display an operation display which is described in a server language such as an HTML which is transmitted from the endoscope device 1 as a GUI. Also, the external terminal 21 which is connected to an external network of Internet which links to the network can also perform an image display operation and a remote operation.

Also, the remote control device 2 can be connected to the external terminals 18 and 21 via the network. The main remote control device 2 can access to the external terminals 18, 21 on which the Web server is carried among these external terminals so as to display a recorded examination image, an examination datum, a manual instruction and a measurement result, drawings for examined section of the sample object on the WWW (Web) browser on a display of the main remote control device 2 appropriately. By doing this, for example, if the information which is stored in the external terminal which is disposed in a remote place while the examination is performed, it is possible to obtain the necessary information by the main remote control device which is disposed in the remote place so as to display the necessary information at the examination site.

Figure 4:
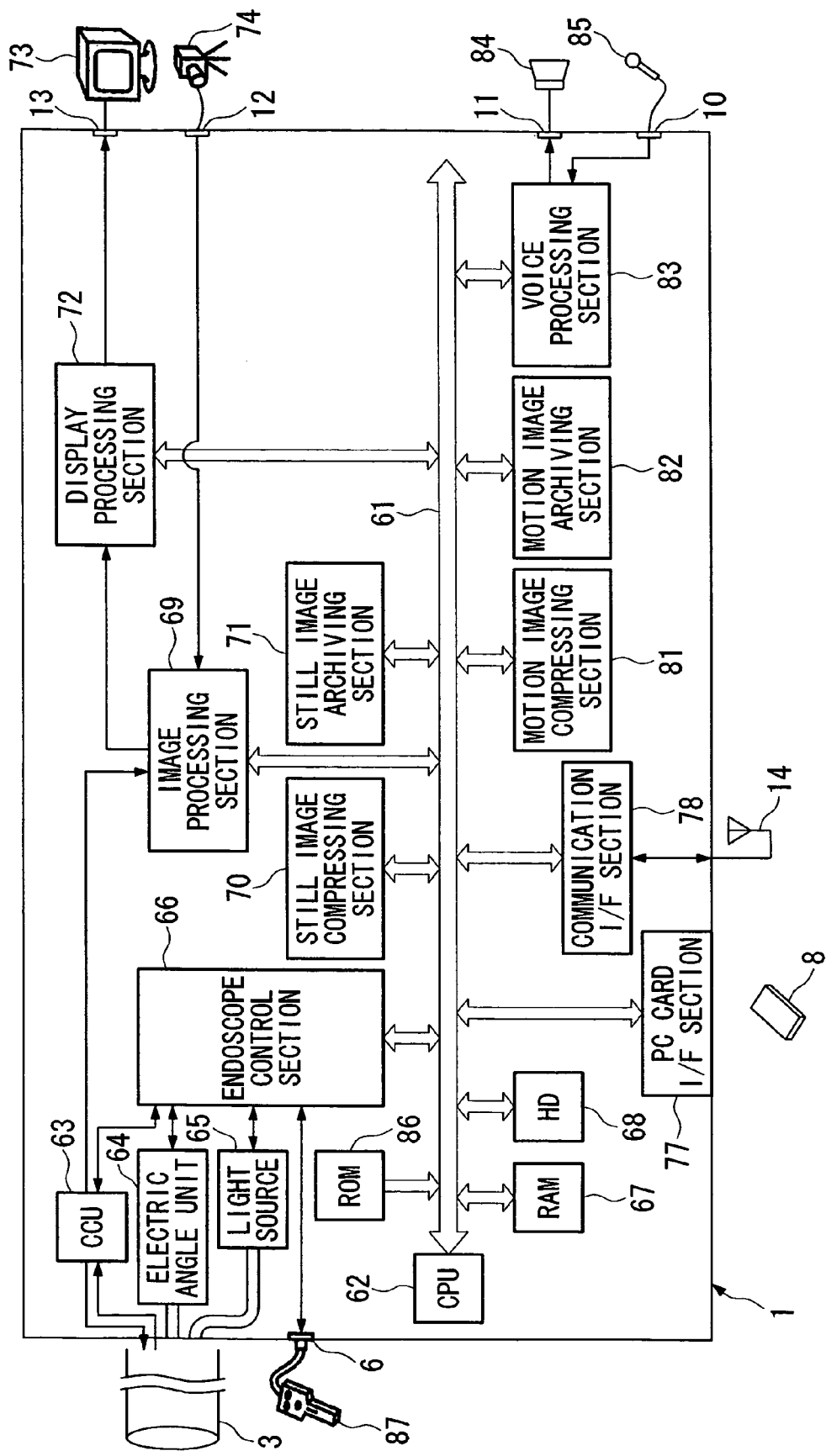
FIG. 4 is a block diagram for showing an inner structure of an endoscope according to the first embodiment.

FIG. 4 is a block diagram for showing an inner structure of an endoscope according to the first embodiment.

The endoscope device 1 is provided with a camera control unit (CCU) 63 for controlling the CCD which is disposed on a tip of the insertion section 3 so as to capture an endoscope image and input the captured image, an electric angle unit 64 which controls a bending movement of the tip of the insertion section 3, and a light source 65 for emitting a light into an inside of the sample object such that these members are controlled by the endoscope control section 66. The endoscope control section 66 is controlled by the CPU 62 via an inner bus 61. The inner bus 61 is connected to an inner section such that an entire inner bus 61 can be controlled by the CPU 62. Also, the endoscope device 1 is controlled by connecting another remote control device (a wired main remote control device 87) to a remote control device connection section 6 if a wireless communication cannot be used because of a condition for observing the sample object. Also, the communication I/F function is provided in the endoscope image control section 66 such that the endoscope control section 66 can communicate the CCU 63, the electric angle unit 64, a light source 65, and the remote control device 87 so as to control each member. For such a communication I/F function, for example, it is possible to name an RS-232C.

Also, the image processing section 69 selects either one between the endoscope image from the CCU 63 or the image which is captured by the camera 74 which is connected to the external image input section 12 according to a setting such as a menu in the GUI and performs an A/D conversion. Furthermore, the image processing section 69 performs various image processing such as a trimming operation and an adjustment for brightness so as to output such image to the display processing section 72 or contain the image in an RAM 67 via an inner bus 61. When the image is contained in the RAM 67, there may be a case in which an image is compressed as explained later. The display processing section 72 displays the image datum in which a graphic is overlapped on an image which is read out from the image from the image processing section 69 or the RAM 67 in a display device 73 such as a monitor via an external terminal 13.

The endoscope device 1 is provided with a ROM 86 in which an application program for performing various processing operations such a program for establishing an endoscope device 1, other control program and an application software for controlling the driving operation for the endoscope, a hard disk (HD) 68 in which an information such an image and a measurement result etc. are stored, and a PC card I/F section 77 which records in a PC card 8 or reads out program and an information which are similar to the HD 68 from the PC card 8.

Furthermore, an antenna 14 is provided for a wireless communication for connecting to the network (wireless LAN) by using the wireless communication method, a network connection terminal 22 for connecting to eh network (wired LAN) by using the wire communication method such that the information which is transmitted to the network 19 among the image which includes an endoscope image and an image which is captured by the camera 74 and the voice are processed by the communication I/F section 78. In the communication I/F section 78, the signal is converted so as to be suitable for a wireless communication or a wired communication and transmitted. On the other hand, the signal is converted so as to be suitable such that the CPU 62 can process the received data and transmit the converted data to the inner bus 61. When an image or an operation image are transmitted via a network 19, an image which is contained in a RAM 67 and a file which is described n a server language such as an HTML are transmitted.

In addition, in an image which includes an image which is captured by a camera or an endoscope image, a still image compressing section 70 for operating an image compressing process for a still image and a motion picture compressing section 81 for operating a process for compressing the motion picture are provided. In such a method for compressing the image, for example, a signal is compressed by a compressing method for realizing a variable-length code by an orthogonal conversion code such as a DCT (Discrer Cosine Transform) method such that the image data for the compressed still image and the motion image are stored in the RAM 67. Also, the still image which is read out (compressed) from an image data which is received by a communication or a RAM 67 is archived by a still image archive section 71 so as to be restored. Also (compressed) a motion image is archived by a motion picture archive section 82 so as to be restored under an initial condition. For such a still image, a JPEG or a JPEG2000 are known. For an example for a compressed motion image, it is possible to name MJPEG, MPEG-2, and MPEG-4. Also, a voice is collected by a microphone 85 which is connected to a external voice inputting section 10 by a voice processing section 83 such that the voice is emitted from a speaker 84 which is connected to an external voice outputting section 11. The voice processing section 83 performs an A/D conversion processing operation for a voice. The converted voice data are sometimes recorded in an RAM 68 or transmitted from a communication I/F section 78. Also, a D/A conversion for the received voice data and the recorded voice data are performed so as to be emitted from the speaker 84 as a voice.

Figure 5:
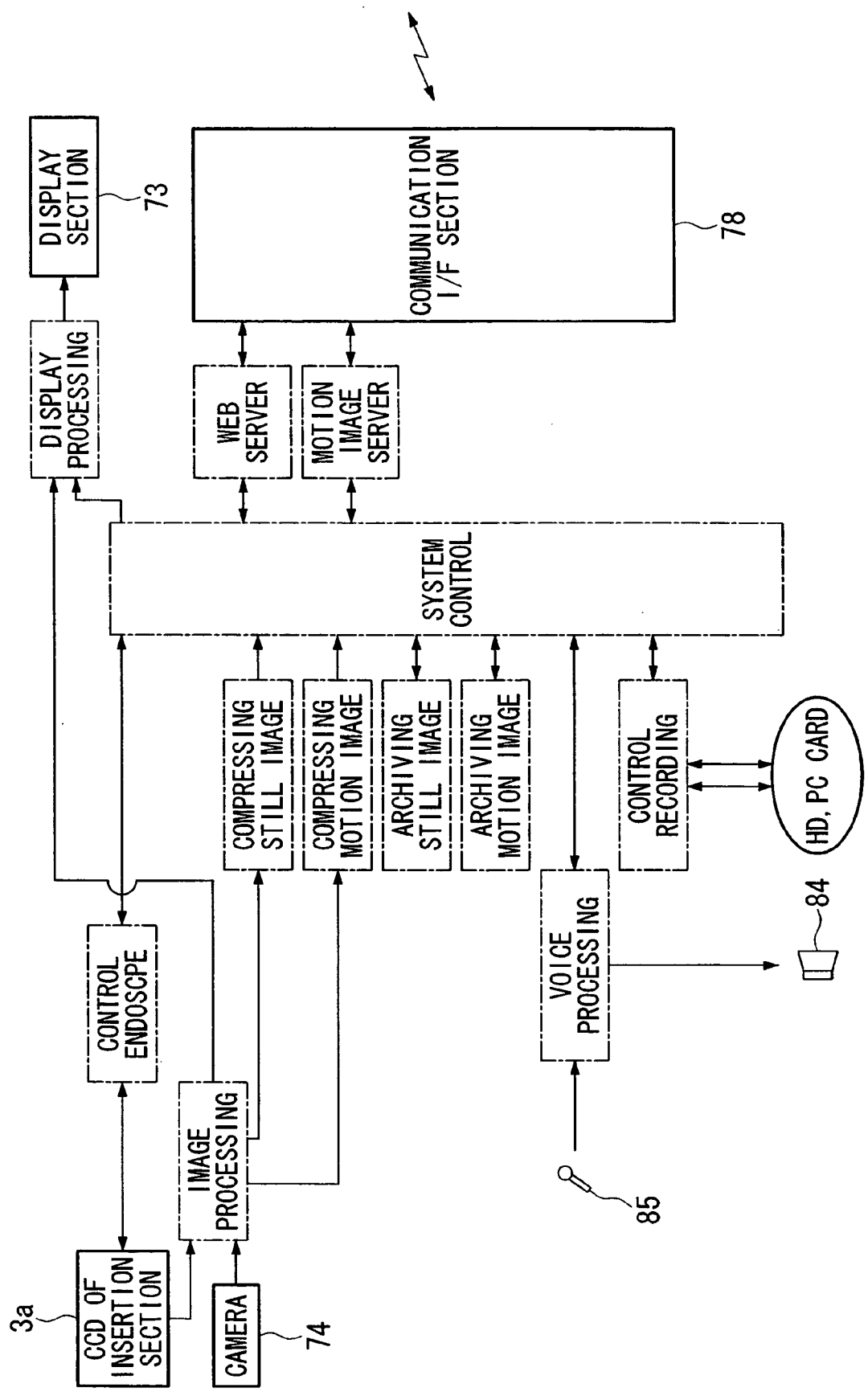
FIG. 5 is a view for explaining an image which includes an endoscope image and a voice datum such as a voice in an endoscope device according to the first embodiment.

Flow of images which include the endoscope image in the endoscope and voice data such as a voice is explained with reference to FIGS. 4 and 5.

First, a CCD3a which is disposed on a tip of an insertion section 3 is driven by CCU 63 according to a setting condition such as a Brightness or a Zoom from an endoscope control section 66 which is controlled by a CPU 62 systematically; thus, the endoscope image (a still image and a motion image) are captured.

Various processing operations such as A/D conversion are performed for these endoscope image and the captured image so as to be generated as image data. Either one of the generated image data are processed so as to be displayed in a display processing section 72. After that the processed image data are displayed in a display section 73 such as a monitor. Here, the image which is captured by a CCD 3a and a camera 30 is processed to be displayed such that the image should not compressed; thus, a graphic which is formed by a CPU 62 is overlapped thereon so as to be displayed in the display section 73.

Also, in addition to the image data, the still image in the image data is compressed to be a sill image in the still image compressing section 70. The motion image is compressed to be a motion image in a motion picture compressing section 81. Thus, each image is stored in a RAM 67 temporarily. If image data are transmitted in a motion picture condition, the image is read out from the RAM 67 so as to be transmitted to a main remote control device 2 or an external terminal 18 via a network by a communication I/F section 78 by using the motion image server. Also, the still image etc. are transmitted together with an operation HTML by a Web server via a network as similarly. In the Web browser, information which is transmitted from the Web server such as a still image, a motion image, an operation display, and a measurement value is displayed such that an instruction from a person who performs the examination for this display is received so as to to transmitted to the Web server. Also, a voice of a person who performs the examination and a sound therearound which are collected by a microphone 85 is processed to be a voice by a voice processing section 83 so as to generate voice data which can be used in a communication. Also inputted voice data are processed to be a voice signal so as to be outputted from the speaker 84. The information such as these image and voice a recorded controllably. These information can be stored in a HD and a PC card.

In the present embodiment, the network communication for such image and voice are performed through a communication I/F section 78. In a wireless LAN network, data are communicated via an antenna 14. Also, a simultaneous mutual communication (telephone communication) for the voice can be realized by using an built-in microphone and a built-in speaker in a main remote control device 2, a microphone and a speaker which are connected to external terminals 18, 21 endoscope device 1 which are connected via a network.

Figure 6:
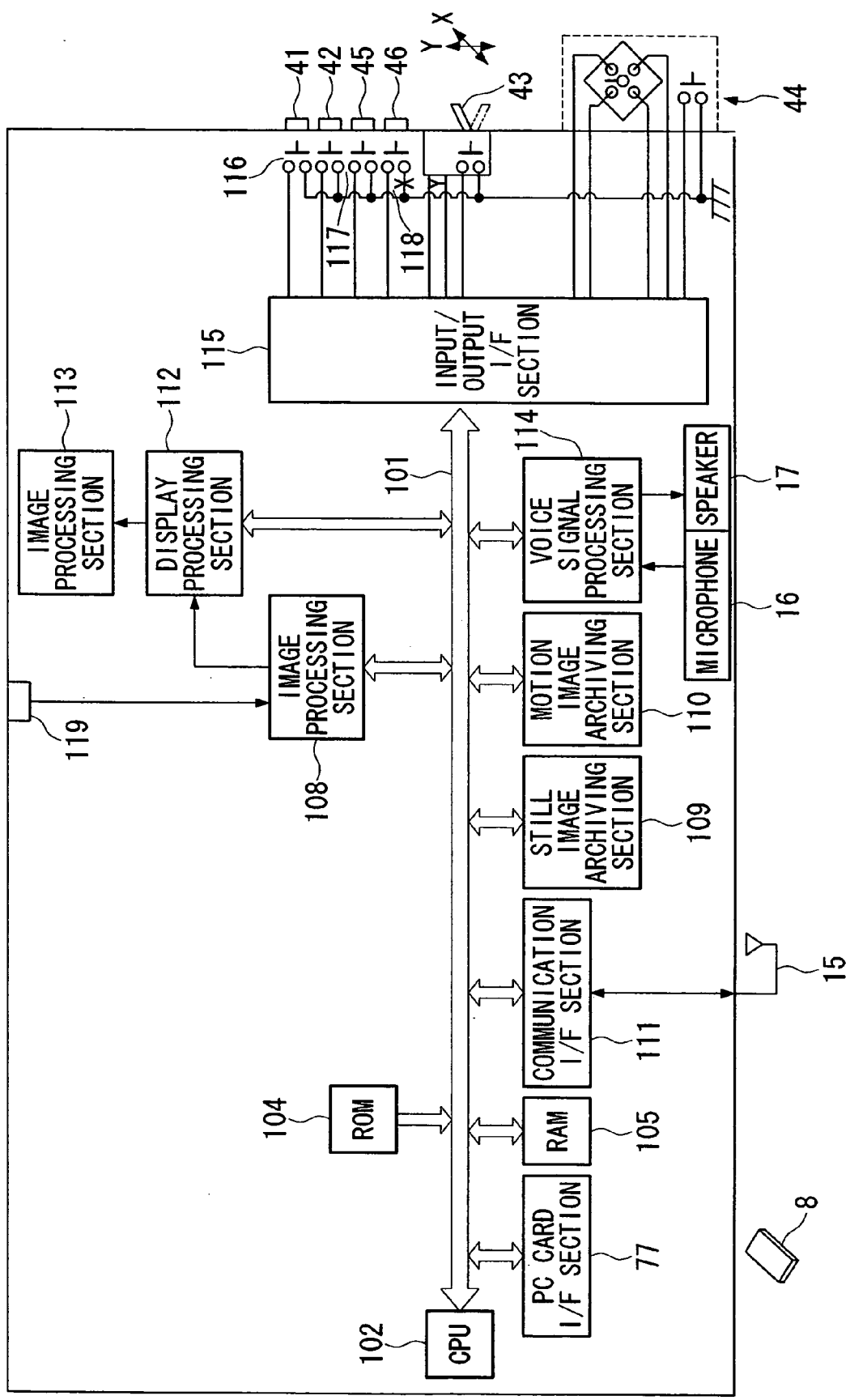
FIG. 6 is a block diagram for showing an inside view for a main remote control section according to the first embodiment.

FIG. 6 is a block diagram for an inner structure of the main remote control device 2.

Each member in the main remote control device 2 is connected to an inner bus 101 so as to be controlled by a CPU 102 through the inner bus 101.

The main remote control device 2 comprises a ROM 104 in which a control program which includes a main remote control device establishing program and a software for performing a various processes, a RAM 105 which contains an endoscope image which is transmitted from the endoscope device 1 and spreads the control program, a still image archive section 109 and a motion image archive section 110 which archive the image which is read out from the RAM 105 or an image (motion image and still image) which is transmitted from the endoscope device 1 so as to restore original images, a voice signal processing section 114 which processes a voice of a person who performs the examination and a voice signal which are collected by a microphone 16 so as to output from the speaker 17, an image processing section 108 which performs various image processes including a trimming process for an endoscope image which is received and archived or read out from a RAM 105 and archived or an image from the external image inputting terminal 119 such that the processed image should be contained in the RAM 105 via the display processing section 112 or the inner bus 101, a display processing section 112 which processes such that the overlapped images can be displayed graphically, an image display section 113 which is formed by a monitor such as a liquid crystal display, and an external image inputting terminal 119 for inputting the image from thereoutside.

The voice signal processing section 114 performs an A/D conversion processing operation for the voice which is inputted by the microphone 16 such that the converted voice data should be stored in the RAM 105 or transmitted by the communication I/F section 111. Also, a D/A conversion for the received voice data and the recorded voice data are performed so as to be emitted from the speaker 84 as a voice.

Also, an input/output I/F section 115 which is connected to an inner bus 101 for performing an input/output processing operation for an instruction signal and a control signal, a zoom switch 116 for performing an on/off operation by operating a zoom button 41, a brightness switch 117 which is turned on/off by operating a brightness adjusting button 42, a live switch 118 which is turned on/off by operation a live button 46, a menu selection button 45, an electrical angle joystick 43, and an instruction switch 44 are provided there, too. These members correspond to the members in the switch section 2b.

By the above structure, the main remote control device can drive the endoscope image by a remote operation so as to obtain an endoscope image which is captured by an image capturing element (CCD) which is attached in the insertion section with the information for the image so as to perform the communication (transmitting and receiving operation) for the information which includes the image by a wireless communication via the network for the endoscope device. Also, if the person who performs the examination cannot determine whether or not there is a stoppage of the device or it is necessary to replace parts for the captured endoscope image, the endoscope device is connected to an external terminal of a person who makes decision (supervisor) who exists in a remote place such that the endoscope and the data which relate to the endoscope are displayed so as to make decision. Also, in such a case, the person who makes decision can operate the endoscope device by herself or himself so as to observe the necessary image.

It depends on a user that how frequently the user uses the graphical user interface (GUI); therefore, there is a case in which the GUI is updated because it is necessary to add a new function. Conventionally, there was a necessity for overwriting the program itself by the operator. However, in the present embodiment, it is possible to record the updated HTML file in the PC card 8 by the external device and insert the PC card 8 in a PC card slot which is assembled in a PC card I/F section 77 in the endoscope device. It is possible to overwrite the HTML file in the HD easily by performing the UPDATE function which is not shown in the drawing.

By doing this, it is possible to change the user interface easily. The user interface was completely the same in the same model conventionally. However, in the present invention, it is possible to customize a display structure for each user so as to use easily.

Figure 7:
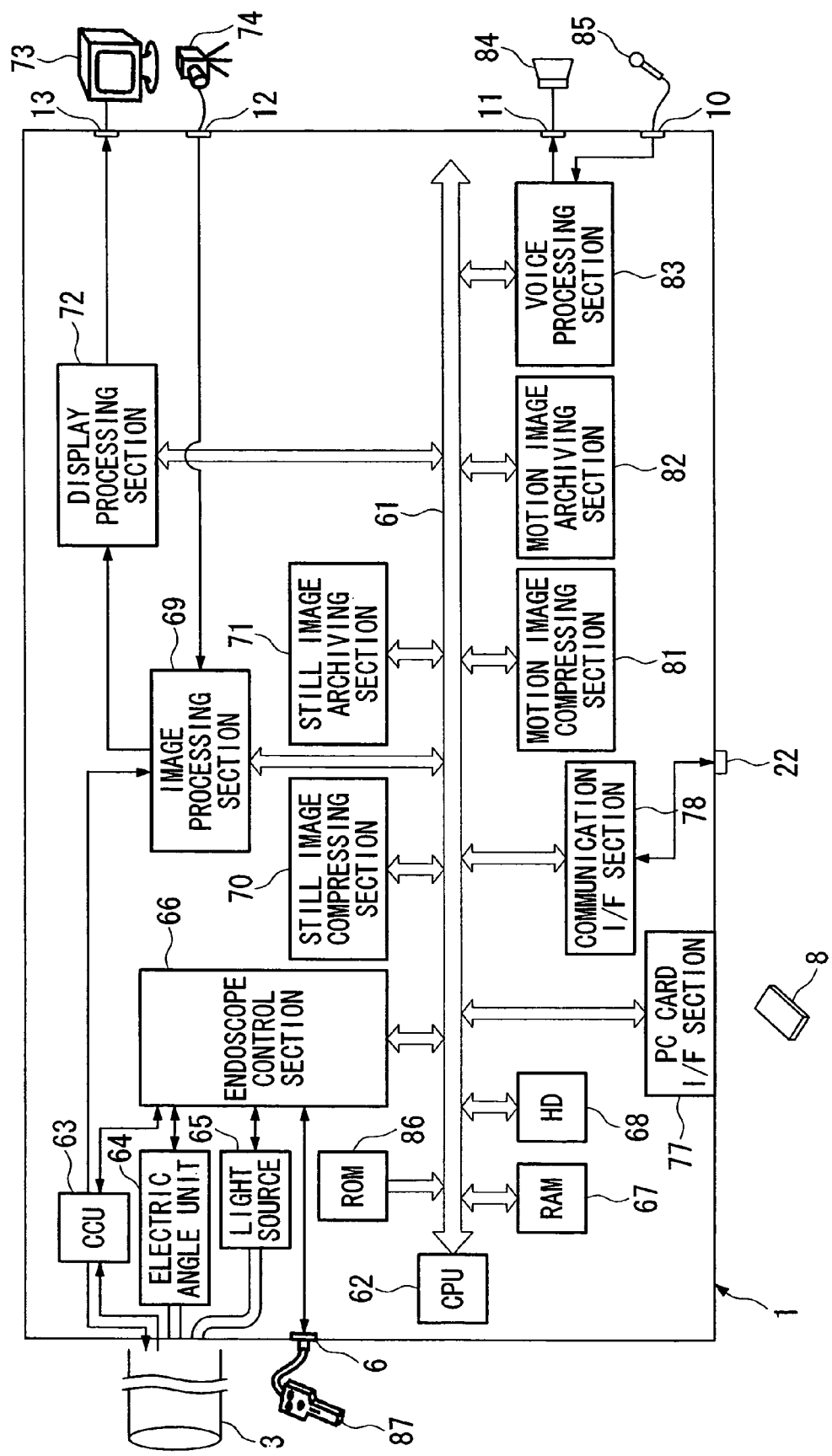
FIG. 7 is a view for a first modified example for an endoscope device according to the first embodiment.
Figure 8:
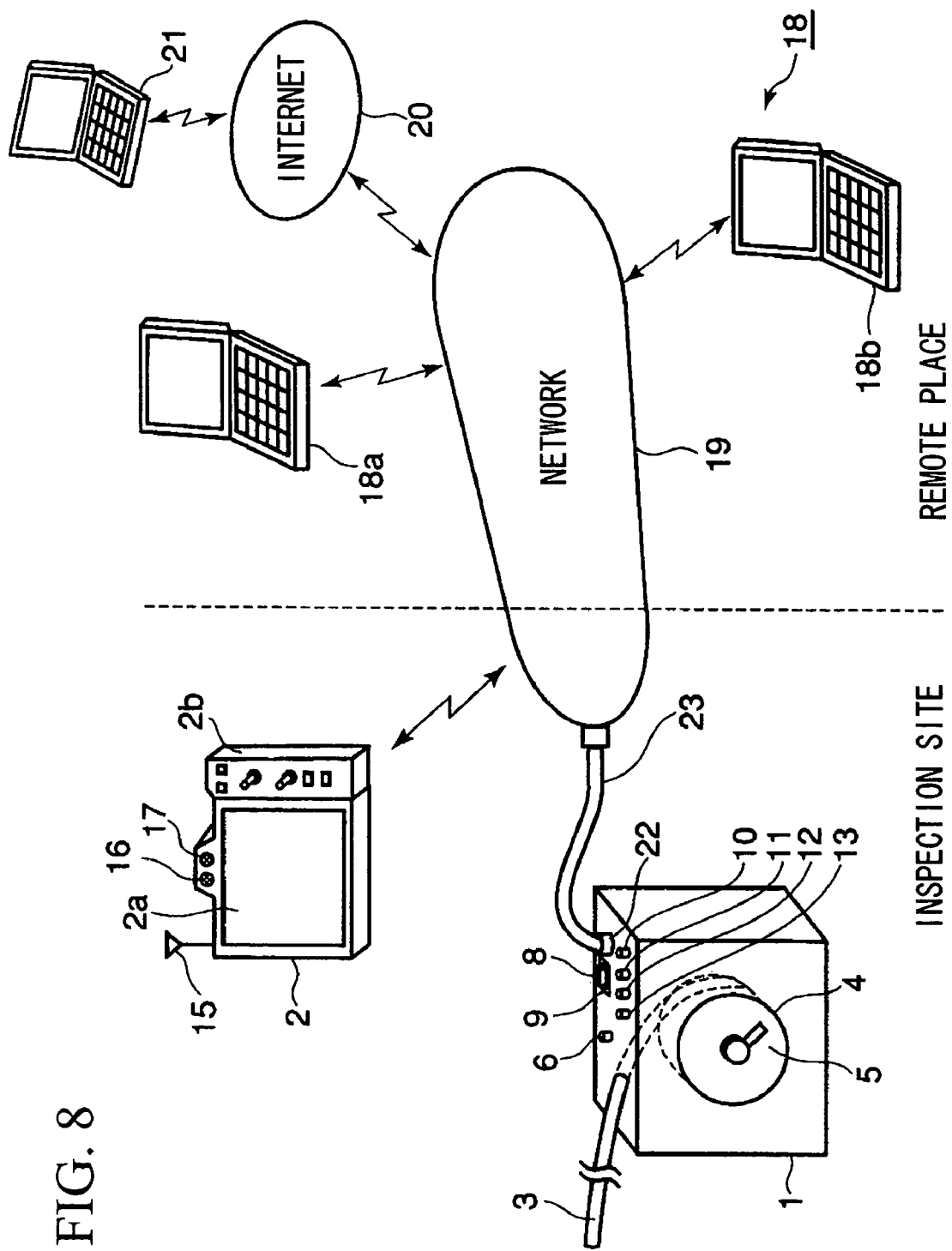
FIG. 8 is a view for showing a general structure of a first modified example of the endoscope according to the first embodiment.

Also, as a modified example for the first embodiment, it is acceptable if a network connection terminal 22 may be disposed as shown in FIG. 7 instead of the antenna 14 when the endoscope device 1 and the network 19 cannot communicate each other by using a wireless communication method. Such a structure corresponds to a structure shown in FIG. 8 in which the network connection terminal 22 is connected to a hub in the network 19 via the connection cable 23.

Also, a simultaneous mutual communication (telephone communication) for the voice can be realized by using an built-in microphone and a built-in speaker in a main remote control device 2, a microphone and a speaker which are connected to external terminals 18, 21 endoscope device 1 which are connected via a network. Here, a method for performing a communication is not limited to a wireless communication method or a wired communication method. That is, it is acceptable if a wireless communication by an antenna 14 and a wired communication by a network connection terminal 22 are compatibly disposed so as to perform both of the communication methods by selecting either one of the method at a site where the examination is performed appropriately.

Figure 9:
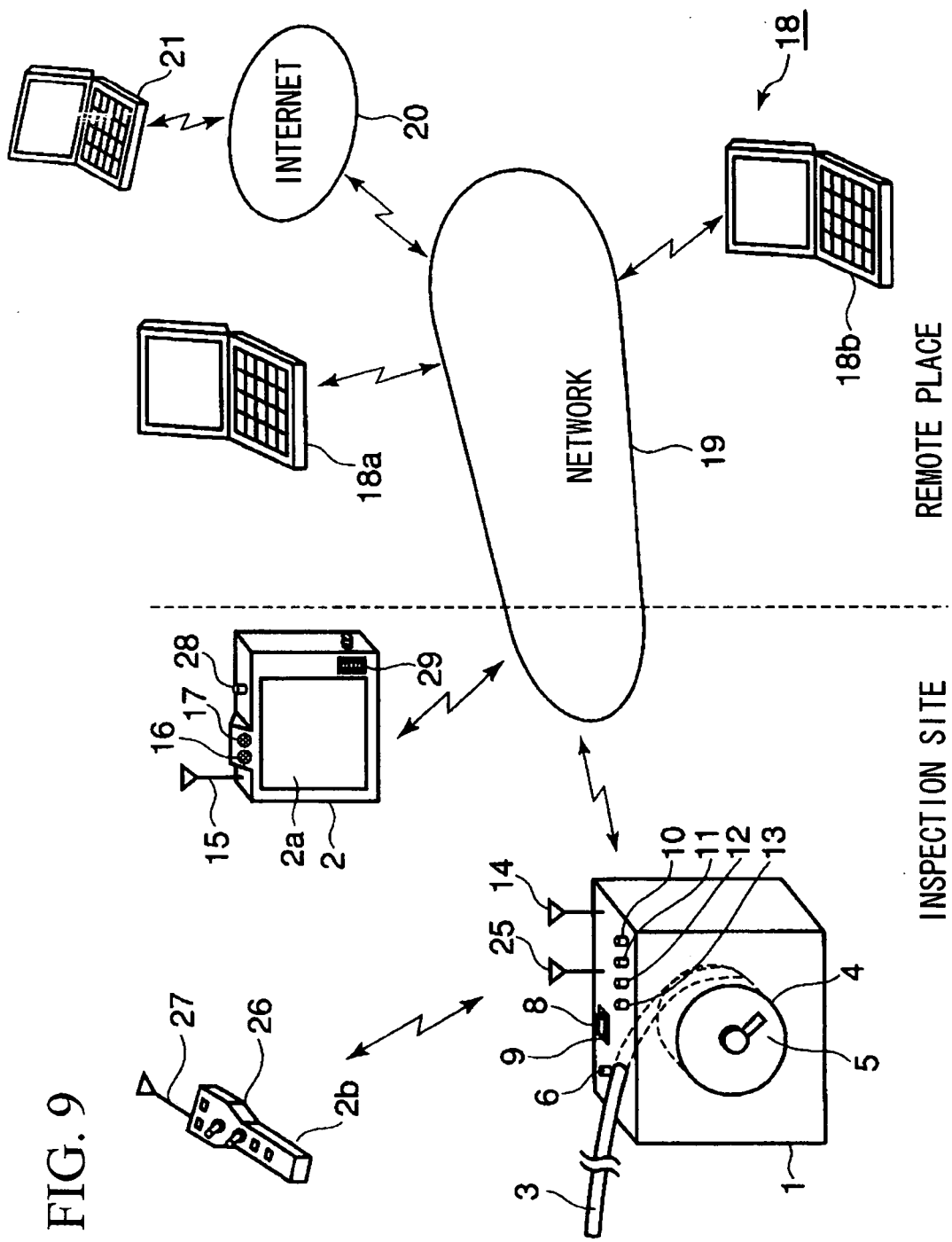
FIG. 9 is a view for a general structure of a endoscope control system according to a second embodiment of the present invention.
Figure 10:
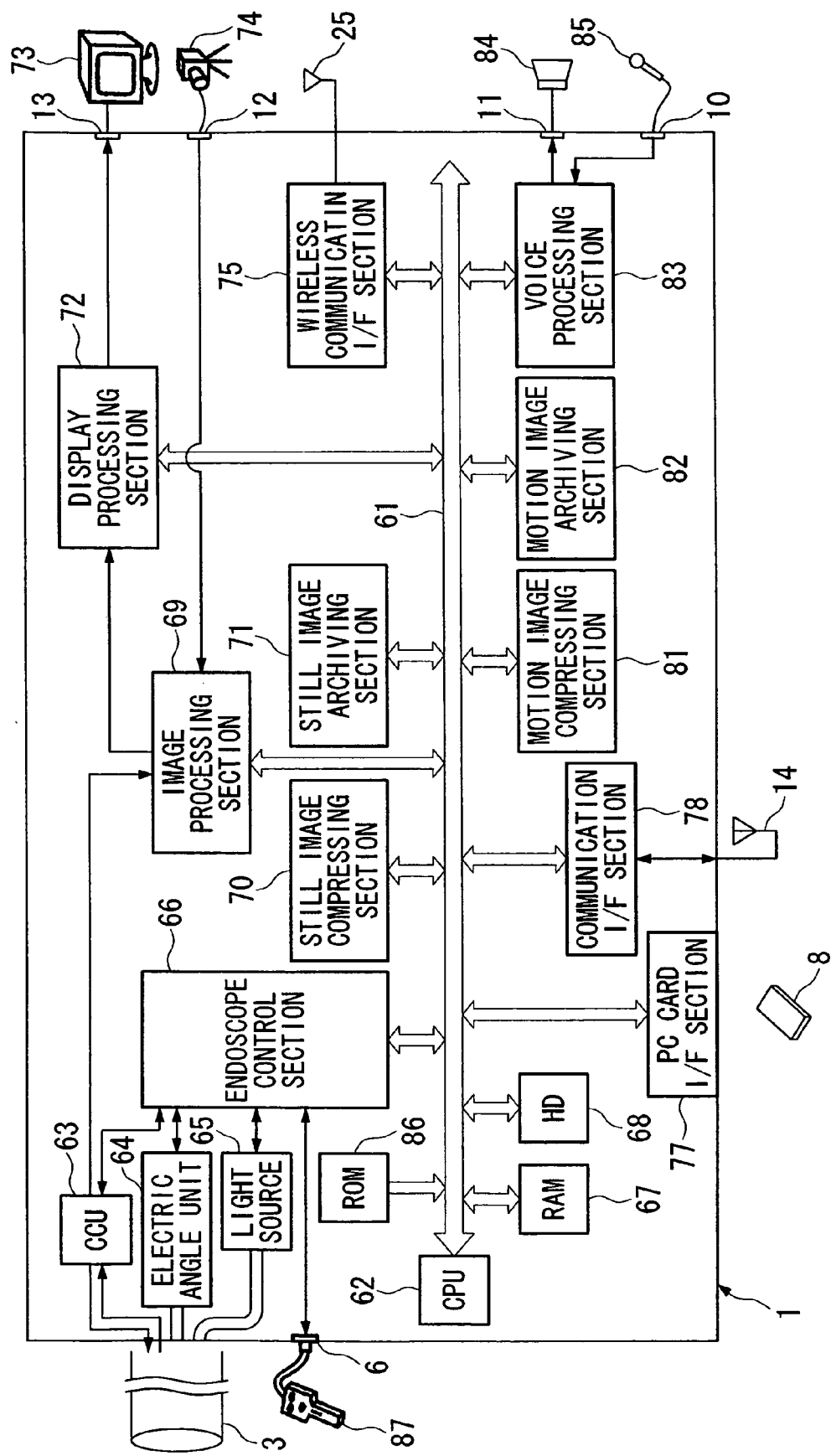
FIG. 10 is a view for showing an inner structure of an endoscope according to the second embodiment.
Figure 11:
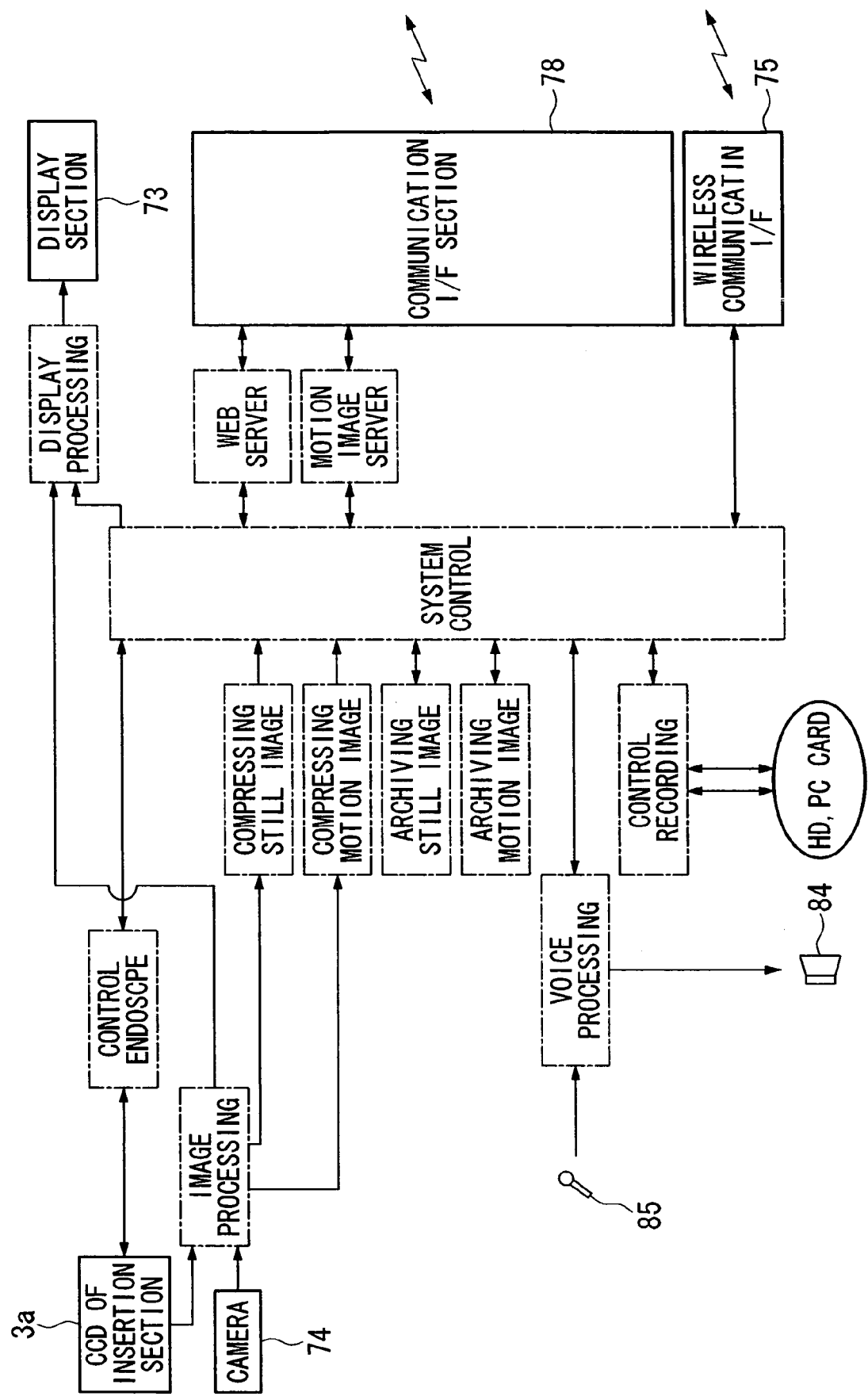
FIG. 11 is a view for explaining an image which includes an endoscope image and a voice datum such as a voice in an endoscope device according to the second embodiment.

FIG. 9 is a view for a general structure of a endoscope control system according to a second embodiment of the present invention. FIG. 10 is a block diagram for showing an inner structure of an endoscope according to the second embodiment. FIG. 11 is a view for showing a flow of an image which includes the endoscope image and voice data such as a voice in the second embodiment. Same reference numeral is add to the member which has been explained in the first embodiment so as to omit the repetition of the explanation. Here, only a characteristic feature is explained.

In the present system, an image display section 2a in the main remote control device 2 in the above explained first embodiment and the switch section 2b are separated. In the present embodiment, a vice-remote control device (hereinafter called a vice-remote control device or an operation switch section) 26 in which a wireless communication function and an antenna 27 are added to this switch section 2b in the endoscope device 1 such that the endoscope device 1 is provided with a wireless communication function for the wireless communication I/F section 75 and the vice-remote control device 26 and an antenna 25 which is used exclusively for that purpose. The vice-remote control device 26 is connected directly to the endoscope device 1 via the antenna 25 in a wireless communication condition so as to transmit an operation signal for performing a driving control operation.

Figure 12:
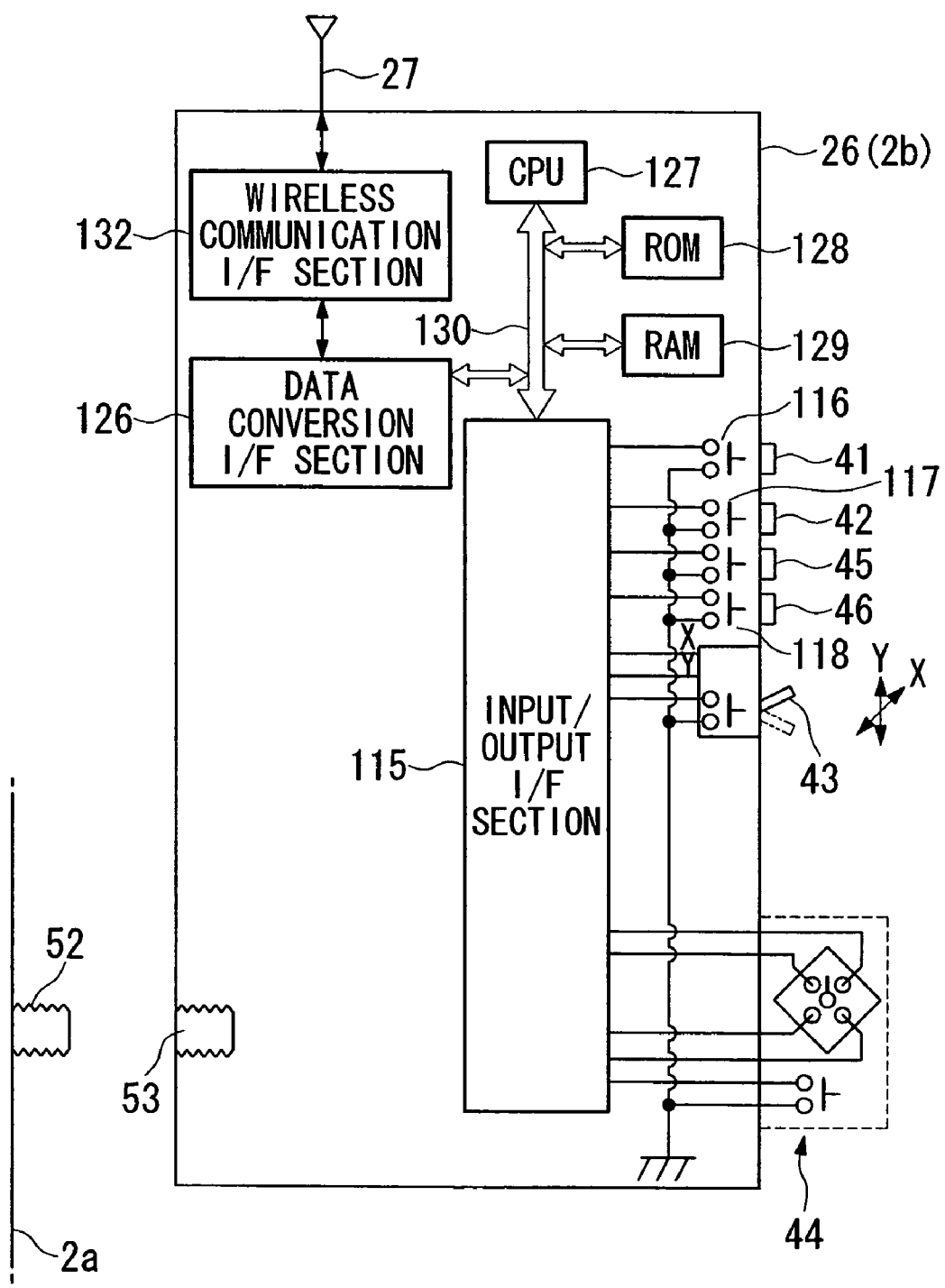
FIG. 12 is a view for showing an inner structure of an subordinate remote control device according to the second embodiment.

FIG. 12 shows an inner structure for the vice-remote control device 26.

Each member in the main remote control device 26 is connected to an inner bus 130 so as to be controlled by a CPU 127 through the inner bus 130. The vice-remote control device 26 is provided with a ROM 128 in which a software is stored for performing a control program which includes a program for establishing a vice-remote control device and various processing operations, a RAM 129 which spreads the program which is read out from the ROM 128 and stores the data which relate to the operation, a data conversion I/F section 126 for performing data conversion for performing a serial communication, and a wireless communication I/F section 132 for performing a wireless communication. In this example, it is acceptable if an RS-232C or a UART (Universal Asynchronous Receiver Transmitter) for the data conversion I/F section 126.

Furthermore, the vice-remote control device 26 is provided with an input/output I/F section 115 for performing an input/output processing operation for the instruction signal and the control signal, a zoom switch 116 which turns on/off by operating the above explained zoom button 41, a brightness switch 117 which is turned on/off by operating the brightness adjusting button 42, a live switch 118 which switches the live image and the freeze image (an image which is formed by stopping a motion image) by operating the live button 46, a menu selection button 45, a electrical angle joystick 43, an instruction switch 44, and further an input/output I/F section 115 which can connect the input/output of on/off operations in these switches to the CPU 127 such that the CPU 127 can process the input/output of the input/output operations. Here, a screw hole 53 is disposed on a side of a casing of the vice-remote control device 26 such that the screw hole 53 engages a fixing screw 52 (a screw shown in FIG. 11) which is disposed in an image display section 2a unitarily.

In such a structure, a person who performs an examination can operate a small-and-light-weight vice-remote control device 26 manually by putting an image display section 2 near her or him; thus an operability improves with compared to a case in which a main remote control device 2 is used.

Figure 13:
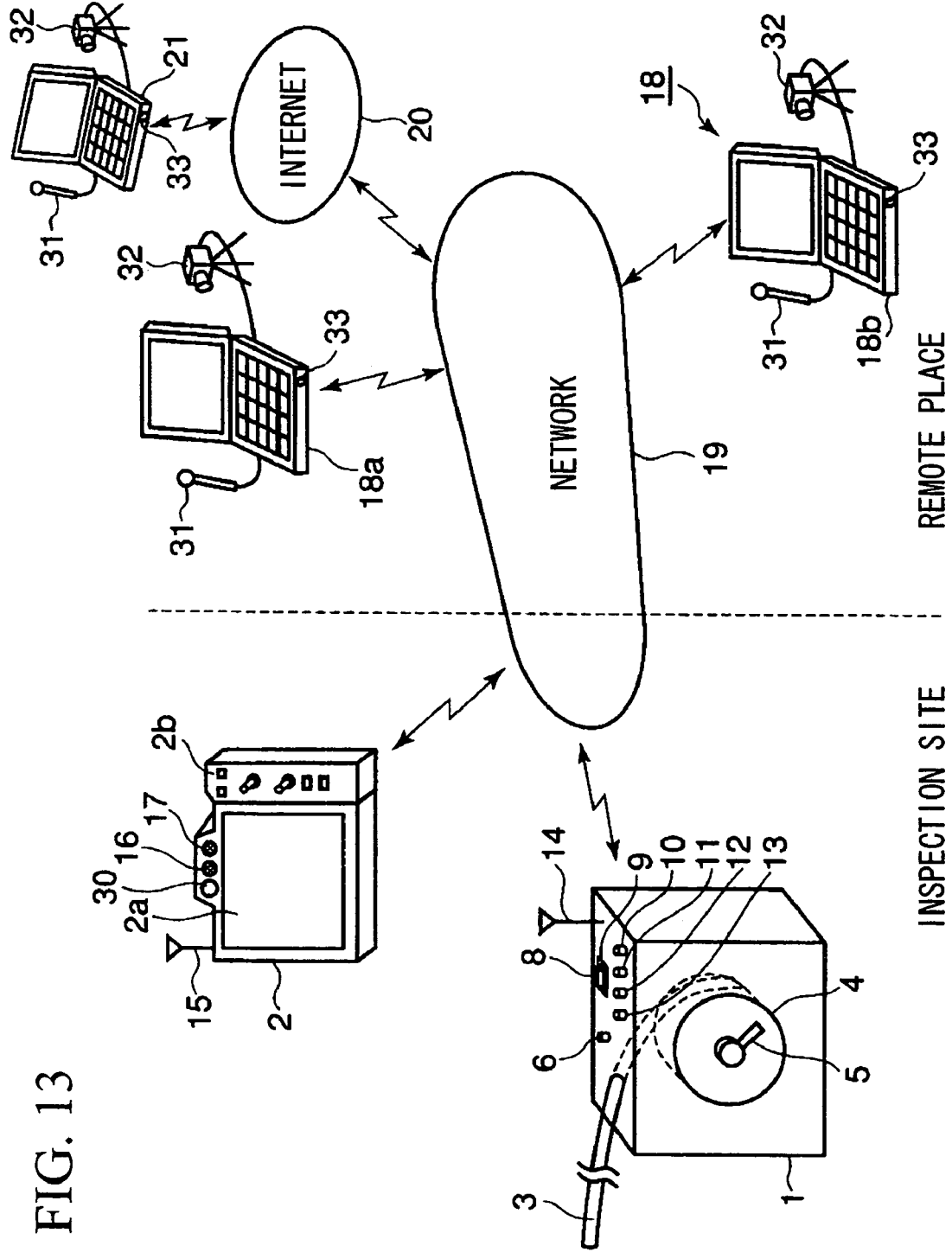
FIG. 13 is a view for a general structure of a endoscope control system according to a third embodiment of the present invention.

FIG. 13 is a view for a general structure of a endoscope control system according to a third embodiment of the present invention.

Figure 3:
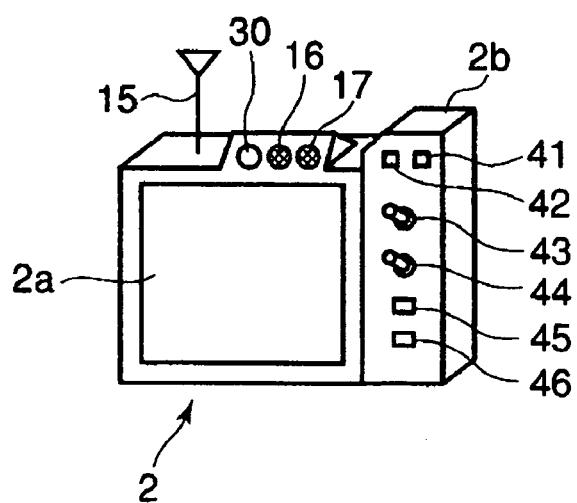
FIG. 3 is an external view for a main remote control section according to a third embodiment.

In this system, a voice of a person who performs an examination and a person who makes decision (observer) and an expression on a face of her or his counterpart and an image therearound are communicated between the main remote control device 2 and the external terminal 18. A camera (image capture) 32, a microphone 31, and a built-in speaker 33 are connected to the external terminal 18. A microphone 16 and a speaker 17 are disposed as shown in FIG. 3 in the main remote control device 2. A built-in electronic camera 30 which is formed by an image capturing optical system and an electronic image capturing element (CCD) is disposed near the main remote control device 2.

Figure 14:
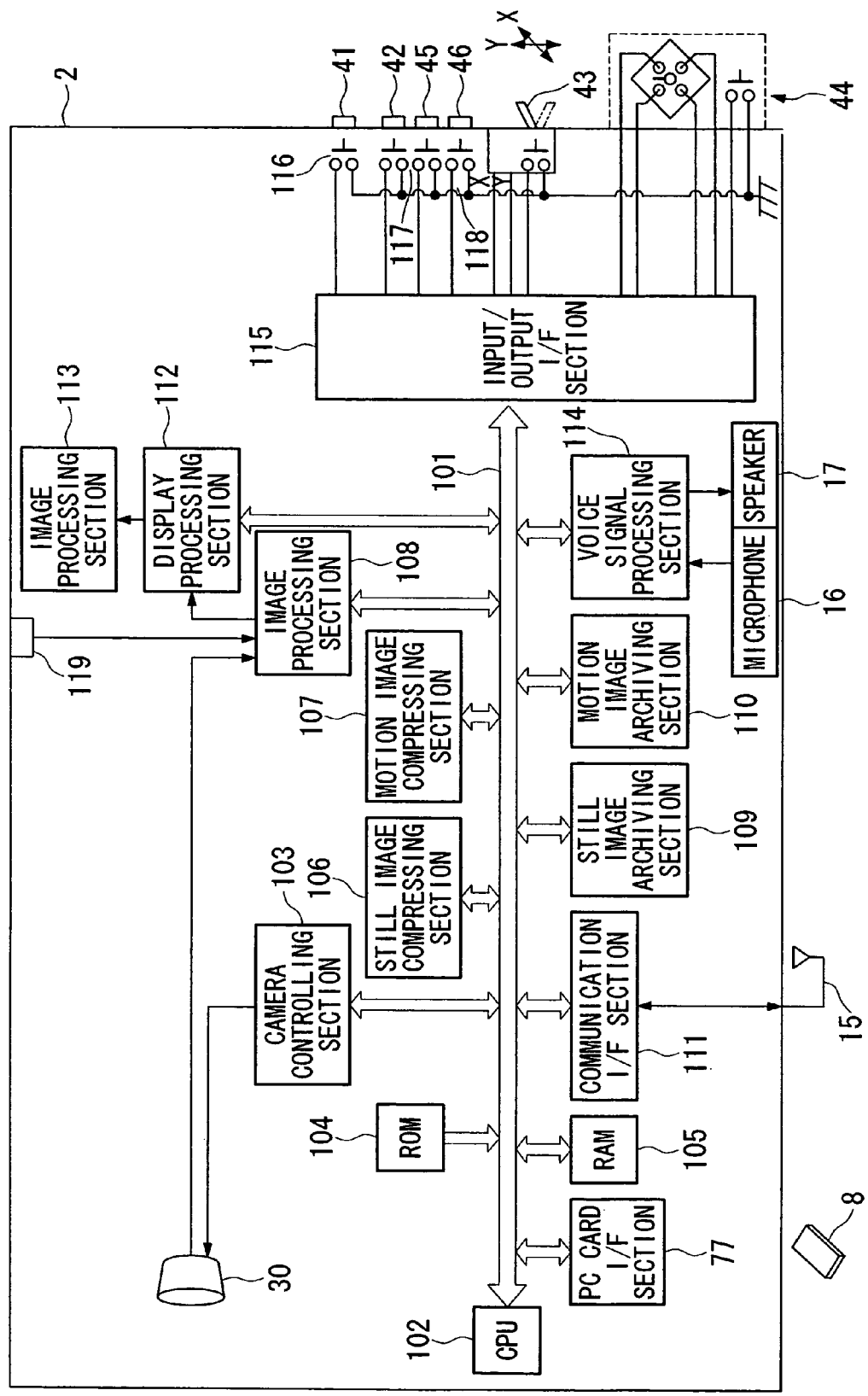
FIG. 14 is a view for an inside view for a main remote control device on which a camera is carried according to a third embodiment.

Explanations are made for an inner structure for the main remote control device 2 in which such a camera is carried with reference to FIG. 14. In addition to the members shown in FIG. 6, a camera 30 which is formed by an image capturing optical system and a CCD, a camera control section 103 for controlling the image capturing operation which includes a controlling operation for an exposure condition for the camera 30, a still image compressing section 106 which compresses the still image among the images which include an expression of a face of the person who performs the examination and captures the image and a condition therearound, and motion picture compressing section 107 which compresses the motion image. Also, the image processing section 108 is provided with a function for performing an image processing operation such as an adjustment for the brightness and a trimming processing operation for the image which is captured by the camera 30. The image which is captured by the camera 30 is not compressed but displayed in the image display section 113.

By such a structure, it is possible to transmit an intention in the communication from one side to the other side more easily and reliably; thus, the other side in the communication can understand the transmitted intention more easily by transmitting and receiving the collected voice and captured image together with the endoscope image during the communication.

Figure 15:
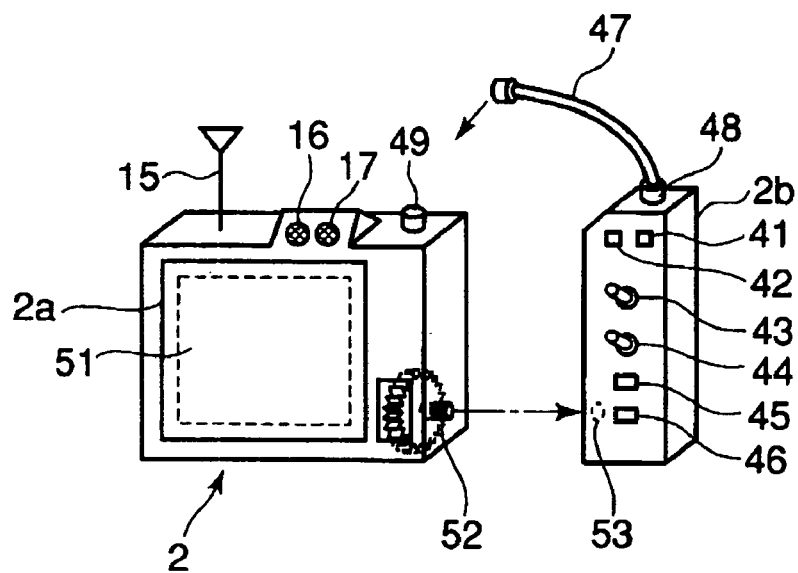
FIG. 15 is a view for a general structure of a main remote control device in a remote controllable endoscope control system according to a fourth embodiment of the present invention.

FIG. 15 is a view for a main remote control device 2 in a general structure of a endoscope control system according to a fourth embodiment of the present invention.

The main remote control device 2 is formed by an image display section 2a which has a similar function with a case which is explained for FIG. 2, and a switch section 2b which can be separated from the image display section 2a. A touch panel 51 is disposed on a display surface of the image display section 2a. It is possible to instruct an inputting operation by pushing an item which is displayed in the display surface on the touch panel 51. Also, a fixing screw 52 is disposed on a side surface of the image display section 2a such that the screw section of the fixing screw 52 is rotative. A screw hole 53 is disposed on a side surface of the switch section 2b such that the screw hole 53 engages the screw section. The image display section 2a and the switch section 2ba are unified by the engagement by the screw and the screw hole. Also, a connector 48 is disposed on an upper surface of the switch section 2b. Also, a connector 49 is disposed on an upper surface of the image display section 2a. These connectors are connected by a cable 47 electrically.

Figure 17:
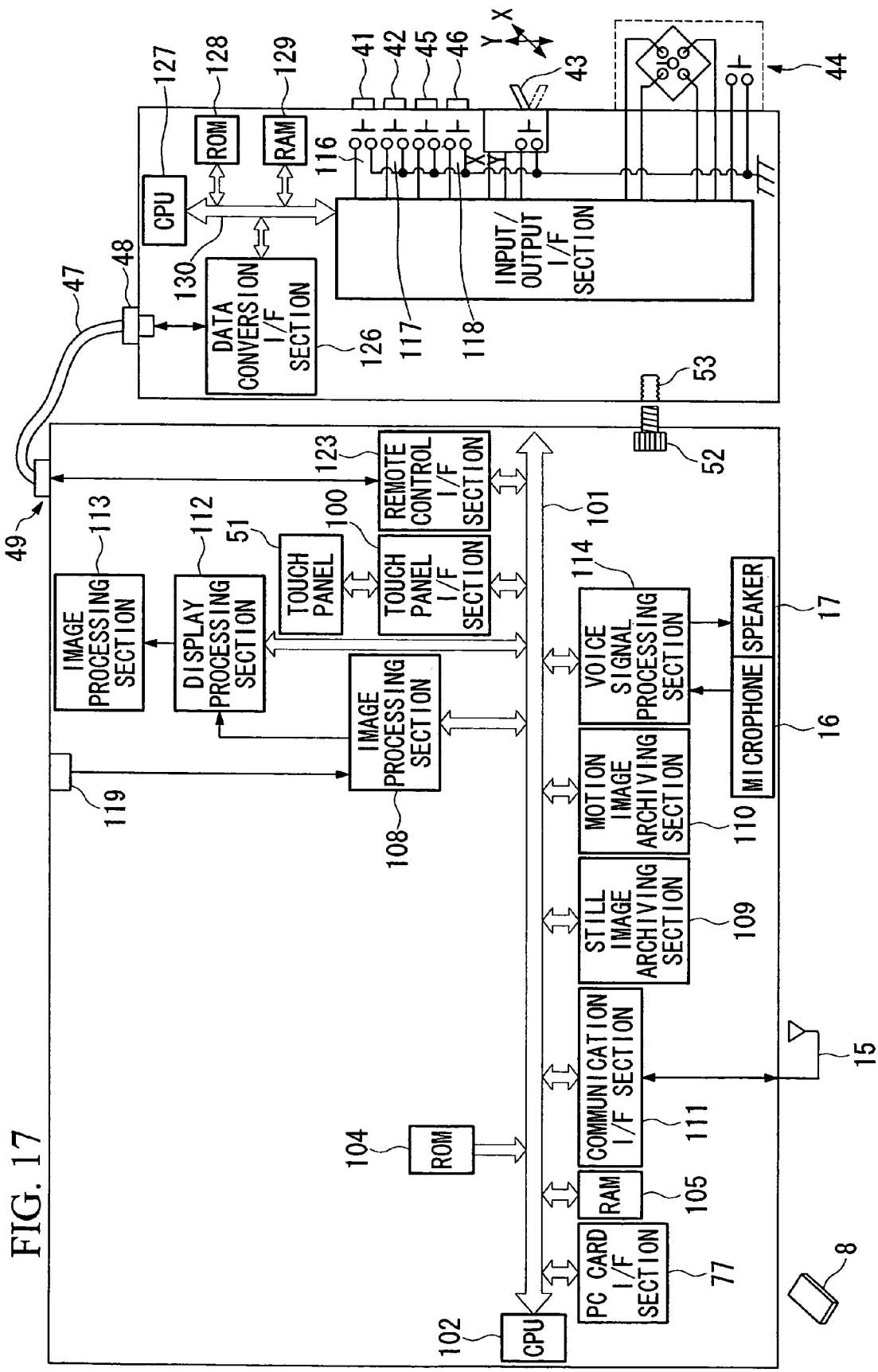
FIG. 17 is a block diagram for showing an inside structure for a main remote control section according to the fourth embodiment.

FIG. 17 is a block diagram for showing an inner structure of an main remote control device according to the fourth embodiment.

Each member in the image display section 2a is connected to an inner bus 101 so as to be controlled by a CPU 102 through the inner bus 101.

The image display section 2a comprises a ROM 104 in which a control program and a software are stored in advance for performing various processing operations, a RAM 105 which contains an endoscope image etc. which is transmitted from the endoscope 1, a still image archive section 109 and a motion picture archive section 110 which archive the image which is read out by the RAM 105 or the image (a motion image and a still image) which is transmitted from the endoscope device 1 by the wireless communication and restores them into initial image, and a voice signal processing section 114 which performs a processing operation for a vice etc. of the person who performs the examination which is collected by the microphone 16 and the received voice signal so as to output from the speaker 17.

The image display section 2a further comprises an image processing section 108 which performs various image processing operations such as a trimming processing operation for the endoscope image which is received or recorded and an image which is transmitted from the external image input terminal 119 and contains the processed image in the RAM 105 via the display process section 112 or the inner bus 101, a display processing section 112 which performs a processing operation for displaying an image, a image display section 113 which is formed by a monitor such as a liquid crystal display element etc., a touch panel 51 which is disposed on a display of the image display section 113, a touch panel I/F section 100 which performs a processing operation for a signal which is inputted by pushing the touch panel 51, a remote control I/F section 123 which communicates with the switch section 2b for the control signal etc., and a connector 49 which connects to the switch section 2b electrically.

Also, the switch section 2b has approximately the same structure as the structure in the vice-remote control device 26 which is explained with reference to FIG. 12. Here, same reference numerals are added to members which have similar feature so as to omit duplicated explanations. The switch section 2b does not have a wireless communication I/F section 132 and an antenna 27. Instead of these members, the switch section 2b is provided with a connector 48 for performing an input/output operation for the data conversion I/F section 126. The switch section 2b is connected with the image display section 2a electrically by connecting the connector 49 via a cable 47. Also, it is acceptable if the cable 47 may be connected to a connection section 6 for a remote control device which is disposed in the endoscope device 1 for operation. Also, the data conversion I/F section 126 and the remote control I/F section may be formed by a serial communication such as an RS-232C.

By such a structure, it is possible to operate the switch section 2b by connecting the image display section 2a and the switch section 2b via a cable separately if it is not possible to perform a wireless communication near the sample object. Therefore, the entire device may be formed in small size and a light weight manner; thus, an operability may be improved with compared to a case in which a main remote control device 2 is formed such that the image display section 2a and the switch section 2b are unified.

Figure 16:
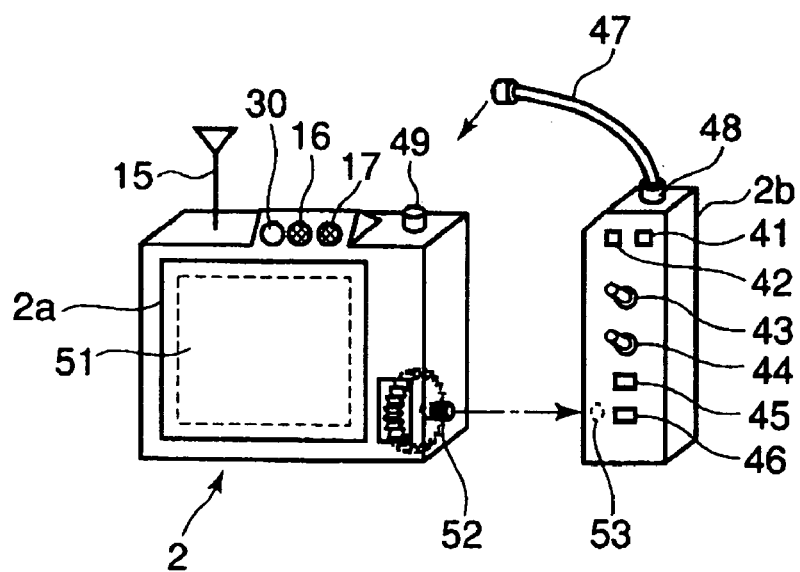
FIG. 16 is a view for a general structure for a main remote control device as a modified example of the fourth embodiment.

FIG. 16 is a view for a general structure for a main remote control device as a modified example of the fourth embodiment. This modified example is formed by an image display section 2a which has a similar function with a case which is explained for FIG. 3, and a switch section 2b which can be separated from the image display section 2a. The rest of the structure is approximately the same as those in the fourth embodiment. Therefore, effects of the present invention can be realized similarly.

In addition to the members shown in FIG. 17, this inner structure is provided with a camera 30 which is formed by an image capturing optical system and a CCD, a camera control section 103 for controlling the image capturing operation which includes a controlling operation for an exposure condition for the camera 30, a still image compressing section 106 which compresses the still image among the images which include an expression of a face of the person who performs the examination and captures the image and a condition therearound, and motion picture compressing section 107 which compresses the motion image. Also, the image processing section 108 is provided with a function for performing an image processing operation such as an adjustment for the brightness and a trimming processing operation for the image which is captured by the camera 30.

Figure 18:
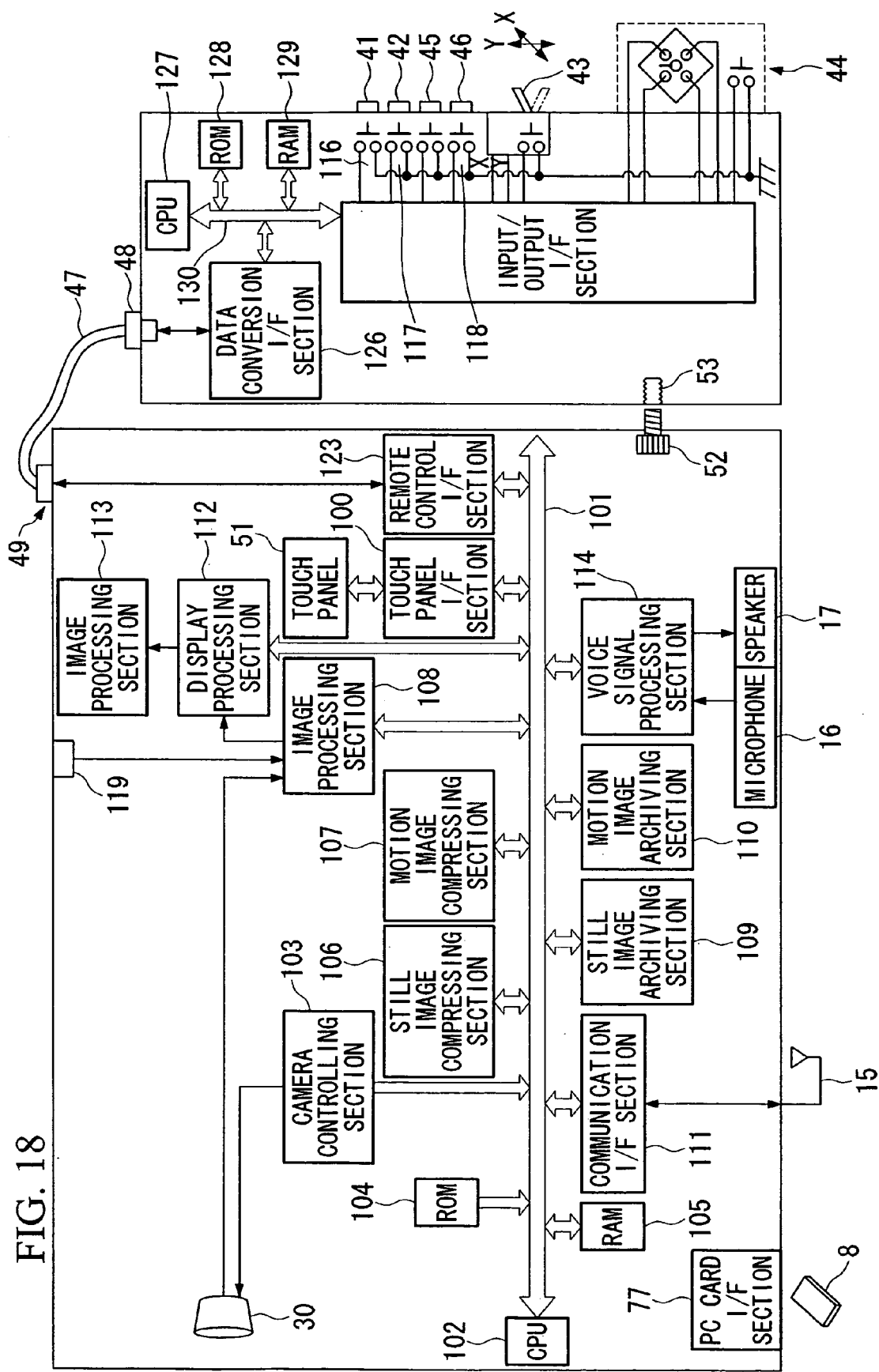
FIG. 18 is a block diagram for showing an inside structure for a modified example for a main remote control device according to the fourth embodiment.
Figure 19:
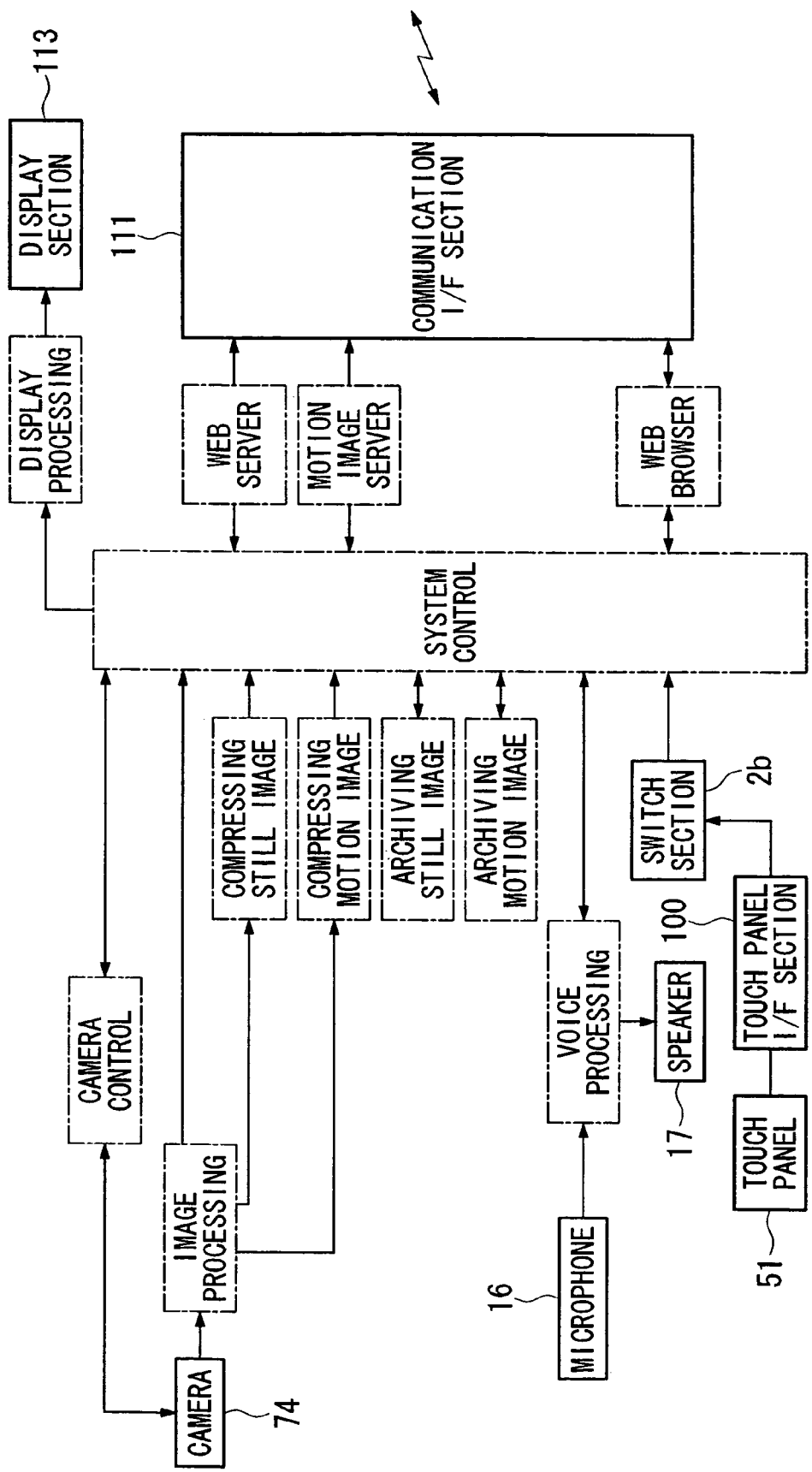
FIG. 19 is a view for explaining an image which includes an endoscope image and a voice datum such as a voice in a modified example of an endoscope device according to the fourth embodiment.

Next, explanations are made for flow of data such as an image for the main remote control device on which a camera shown in FIGS. 16 and 18 is carried and a voice etc. with reference to FIG. 19.

The endoscope image which is inputted from the communication I/F section 111 via the network and the information (HTML etc.) which relates to the inputted image are inputted to the Web browser by the instruction from the switch section 2b such that the inputted compressed data are archived in the still image archive section 109 and the motion picture archive section 111 so as to be the image data under an initial condition. That is, the HTML file which is downloaded from the endoscope device 1 and the data which relate to the operation button are displayed on the Web browser which is displayed in the display surface of the main remote control device 2. The main remote control device 2 and the external terminal 18 as clients request the endoscope device 1 for the data by operating the GUI on the Web browser. For such data, it is possible to name data which relate to the HTML and the operation button, a live image, an image which is recorded in the endoscope device, and data for a list of the image engine. These received data are also displayed on the Web browser.

The Web server and a motion picture server are carried only when the main remote control device is equipped with a camera. In this case, the Web server distributes the HTML for displaying the browser on the external terminal and the motion image server transmits the compressed motion image together with the voice when the main remote control device performs a television telephone.

The image data are processed so as to be displayed by the display processing section 112 so as to be displayed in the display section 13. In such a case, the graphic which is formed by the CPU 102 is overlapped by the image so as to be displayed on the display section 113. Also, the voice of the person who performs the examination which is collected by the microphone 16 and the sound therearound are processed so as to be stored in the RAM 105 as voice data. Also, the voice signal of the person who makes decision which is included in the received information is processed in the voice processing section 114 so as to be outputted from the speaker 17. By such a structure, it is possible to operate the switch section 2b by connecting the image display section 2a and the switch section 2b via a cable separately if it is not possible to perform a wireless communication near the sample object. Therefore, the entire device may be formed in small size and a light weight manner; thus, an operability may be improved with compared to a case in which a main remote control device 2 is formed such that the image display section 2a and the switch section 2b are unified.

Also, an image processing operation which includes an A/D conversion operation is performed for the image of the person who performs the examination etc which is captured by the camera 30 which is controllably and systematically driven by the CPU 102 so as to generate image data. Among these generated image data, the still image is compressed by the still image compressing section 106 and the motion image is compressed by the motion picture compressing section 107 so as to be stored in the RAM 105 temporarily. If image data are transmitted in a motion picture condition, the image is read out from the RAM 105 so as to be transmitted to an external terminal 18 and an endoscope device 1 via a network by a communication I/F section 111 by using the motion image server. Also, the still image etc. are transmitted together with an operation HTML by a Web server via a network as similarly.

Figure 20:
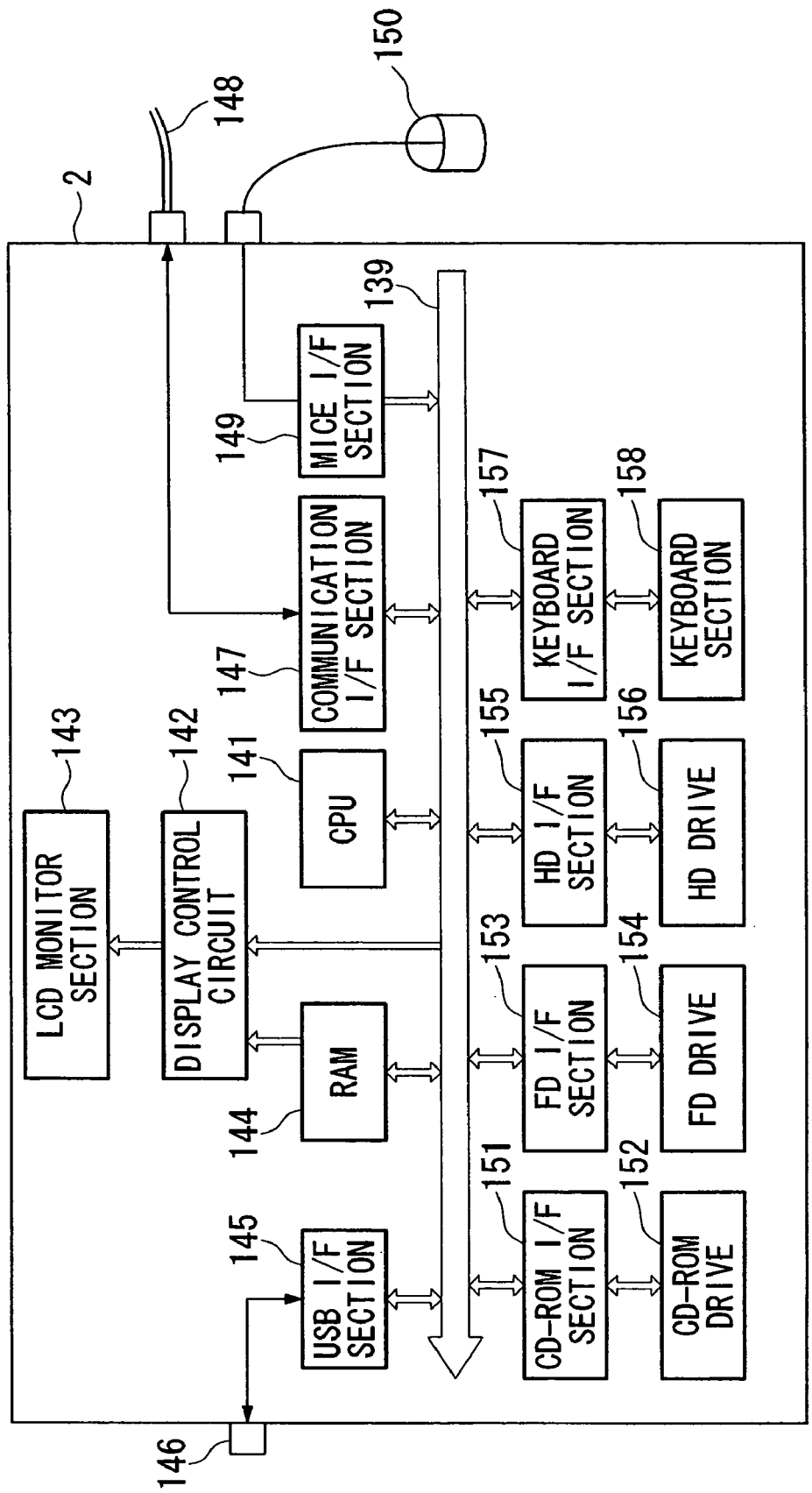
FIG. 20 is a block diagram for an external terminal.

Explanations are made for a block diagram of the external terminals 18, 21 with reference to FIG. 20.

These external terminals are formed by a personal computer etc. In such a structure, each member is connected to an inner bus 139 so as to be controlled by the CPU 141; thus, the signal and the data are transmitted and received.

In these external terminals, a communication I/F section 147 which receives the image data (endoscope image) from the cable 148 and the external terminal 146 via a hub in the network and performs various communication with the endoscope device 1, main remote control device 2, a RAM 144 which serves for a working area in the CPU 141 by spreading the processing programs and contain the received image data, a mice I/F section 149 which is connected to a mice 150 via the external terminal, and a keyboard I/F section 157 which transmits the signal which is inputted from the key board section 158 are connected to the inner bus 139.

Also, a hard disk (HD) drive 156 in which various processing programs are contained, a detachable flexible disk (FD) such as a floppy (registered trademark), and a CD-ROM drive 152 are connected to the inner bus 139 via each interface section (HD I/F section 155, FD I/F section 153, CD-ROM I/F section 151).

Furthermore, a display control circuit 142 which controls the display operation in the LCD monitor section 143 for displaying the image data which are read out by the RAM 144 and various data, and a USB I/F section 145 which is connected to an external terminal 146 which is not shown in the drawing so as to transmit and receive the date according to an USB interface method are provided.

Figure 21:
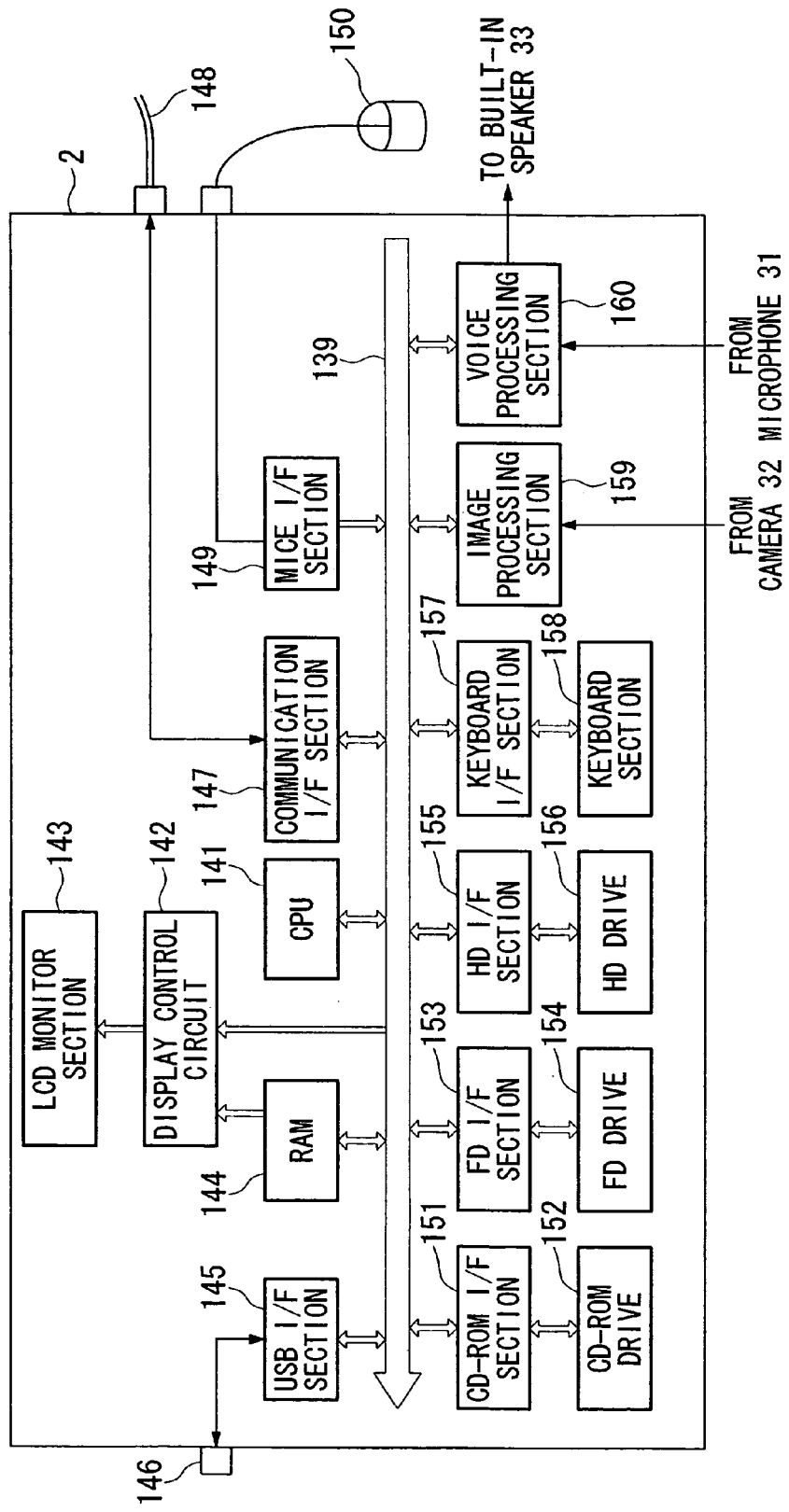
FIG. 21 is a block diagram for a modified example of the external terminal.

Here, if this external terminal is connected with a camera 32, a microphone 31, and a built-in speaker 33 as shown in FIG. 21, an image process section 159 which performs a processing operation for the image which is captured by the camera 32 and a voice processing section 160 which performs a processing operation for the voice which is collected by the microphone 31 and the voice which is outputted from the speaker 3 are provided.

Next, a browser display which is displayed in the display surface on the main remote control device and the external terminal is explained.

Figure 22:
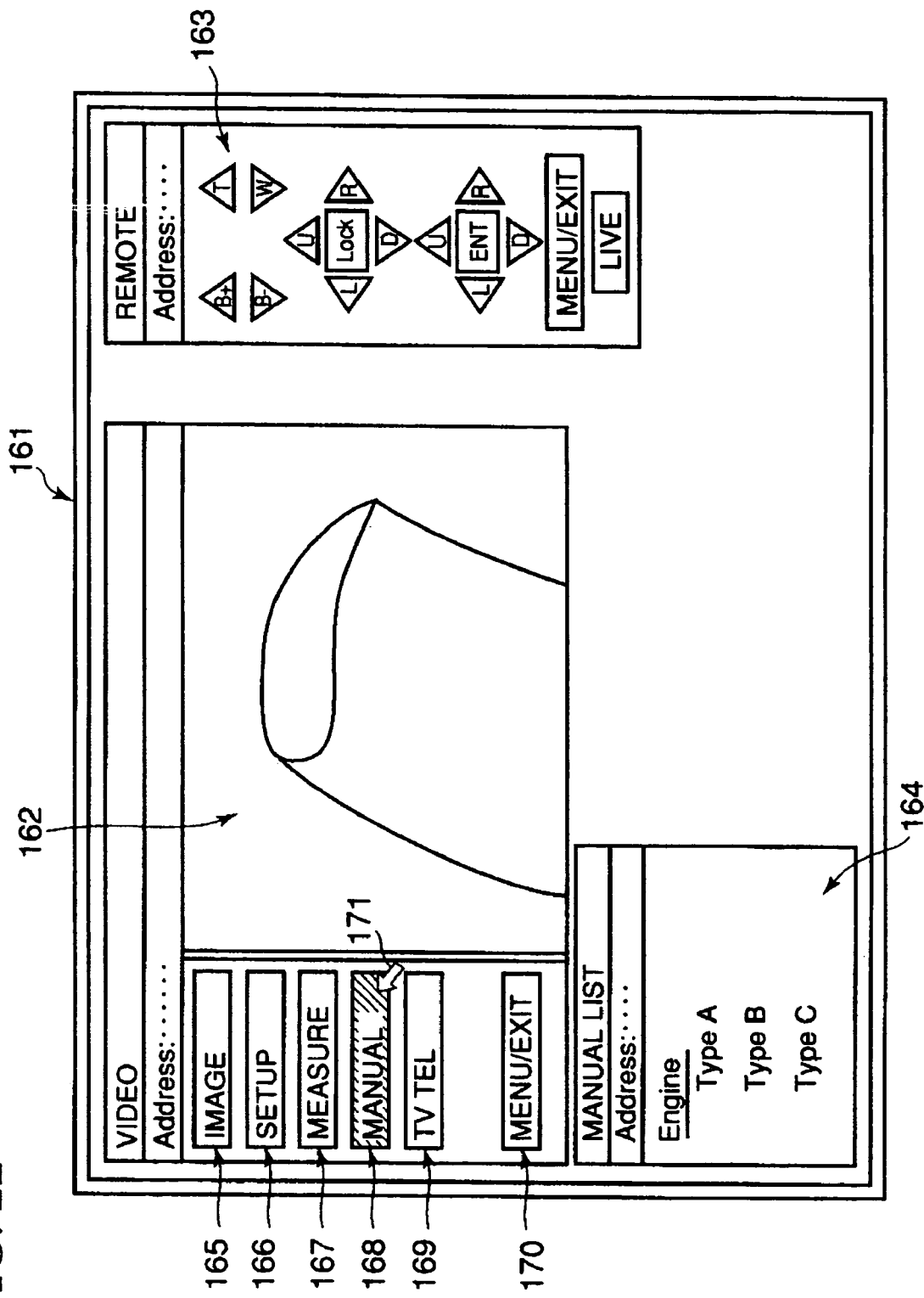
FIG. 22 is an example for a first manual instruction.

FIG. 22 is an example for an inspection manual. A "VIDEO" browser in which an address bar in which a title bar and an URL are displayed, an endoscope image 162 and various menus 165 to 170 are displayed is displayed in this display. A "REMOTE" browser for displaying a remote control panel 163 which resembles the operation panel in the switch section 2b is displayed on a right-hand side of the "VIDEO" browser. Also "MANUAL LIST" browser is displayed so as to display an examination manual beneath the VIDEO browser.

For such various menus, it is possible to name an "IMAGE" menu 165, a "SETUP" menu 166, a "MEASURE" menu 167, a "MANUAL" menu 168, a "TVTEL" menu 169, and a "MENU/EXIT" menu 170.

In the "IMAGE" menu, the image capturing condition such as a shutter speed and an exposure for the camera (CCD) are set and the quality in the displayed image is adjusted. In the "SETUP" menu 166, an initial setting condition for the endoscope device 1 and the main remote control device 2 are set and various setting operations such as a time setting operation are performed.

In the "MEASURE" menu 167, a length and an are of a fault section which is displayed in a image which is captured by the endoscope are calculated. "MEASURE" menu has options which are selectable between a stereo measurement and a comparative measurement. In the stereo measurement, it is possible to measure a length between two points and measure a depth. It is acceptable if such a variation for the measurement may be preset in the "SETUP" menu. Also, it is acceptable if a list for the measurement variation is disposed in the "SETUP" menu 166 so as to select thereamong. Alternatively, it is acceptable if desirable measurement menu is inputted in an address bar.

The "MANUAL" menu 168 serves for a function for downloading and displaying a manual instruction for examining the sample object which is stored in the external terminals 18, 21. The URL for the server in which the instruction manual exists may be preset in the "SETUP" menu 166. Also, it is acceptable if a list for the server in which instruction steps are stored in the "SEETUP" menu 166 so as to select thereamong. Alternatively, it is acceptable if desirable measurement menu is inputted in an address bar.

The "TVTEL" menu 169 is a function for connecting to the external terminals 18, 21 such that the examination display may be discussed by a person who makes decision. The external terminal which is operated by the person who makes decision may be preset in the "SETUP" menu 166. Also, it is acceptable if a list for the address which indicates the terminal of the person who makes decision may be disposed in the "SEETUP" menu 166 so as to select thereamong. Alternatively, it is acceptable if desirable measurement menu is inputted in an address bar.

In the "MENU/EXIT" menu 170, a menu is not displayed and a small icon (not shown in the drawing) for displaying the menu is displayed on the browser. If the menu is not displayed, it is possible to display the endoscope image in a section in which a menu is displayed. Also, it is possible to display in a large display. Furthermore, it is possible to display in an enlarged manner. A small icon for displaying the above explained menu is displayed in a left-beneath section to the image.

In addition to the above manners, it is possible to display an "INDEX" menu, a "RECORD" menu, a "MOVE" menu, a "COPY" menu, and a "DELETE" menu etc.

In the "INDEX" menu, it is possible to display images such as a still image which is stored in the HD or a PC card, a motion image, and a shrunk image which is exists on a server which is connected to the network in an index display manner in another display which is displayed separately.

In the "RECORD" menu, it is possible to store additional information such as a still image, a motion image, a voice, an image, and a measurement result in the HD or the PC card in the endoscope device.

In the "MOVE" menu and the "COPY" menu, it is possible to move additional information such as a still image, a motion image, a voice, an image, and a measurement result which are stored in the HD or the PC card mutually, copy these images, and move/copy these information in the server which is connected to the network.

In the "DELETE" menu, it is possible to delete a still image, a motion image, a voice, an image, and a measurement result which are stored in the HD or the PC card.

Here, explanations are made for the stereo measurement and the comparative measurement in the "MEASURE" menu 167.

In general, a usual adapter is used in which a lens for an image capturing system is disposed on a tip of the insertion section in the endoscope usually. However, if the sample object is measured, it is possible to perform the stereo measurement by using two stereo adapters which are disposed so as to have an interval therebetween so as to obtain an image which has a parallax in the lens for the image capturing system.

When a section which is supposed to be examined is captured by this endoscope, an image which has a parallax is obtained. A three-dimensional coordinate for the image which has a parallax is calculated by using a theory for triangulation. In the stereo measurement, a length and a depth for a flaw is measured by using the three-dimensional coordinate which is obtained in this way such that the measured length and depth are displayed in the display surface and stored such that the measurement result and the image are related. For such a measurement variation for the stereo measurement, there are a "two-point measurement" for measuring the length for the flaw and a "depth measurement" for measuring the depth for the flaw.

Also, the comparative measurement uses a software. If there exists a flaw which is supposed to be measured and an object which has a certain length which has been known in advance (reference length) on an image which is captured by an endoscope, the reference length is determined by inputting the length of the object; thus, the length of the flaw is measured with reference to the reference length so as to display in the display surface. It is possible to store the image and the measured length so as to be related to each other.

In FIG. 22, a "MANUAL" menu is selected and displayed in a converted manner by designating and clicking by a cursor.

When the "MANUAL" menu is selected, a window of "MANUAL LIST" is opened; thus, a server is accessed which contains a manual instruction which is an object as a sample object which is preset according to the above explained method. When a data for the instruction manual is downloaded from the server, for example, a list for the sample objects like a list of "TYPE A" and "TYPE B" (here, example is a jet engine) which are shown in FIG. 22 is displayed.

These "TYPE A" and "TYPE B" are described in a hyper text by the HTML. If each engine is selected, a list for selecting a variation for the turbine of the selected engine is displayed. The list for the turbine is described in a hyper text as similar to a case for the engine; therefore, it is possible to select the section which supposed to be examined in detail. Here, if the "TYPE A" is selected, a display (which is not shown in the drawing) for selecting the variation of the turbine for the "TYPE A" engine is displayed. By selecting the manual instruction in this way, the section which is an object as a sample object is determined. Also, the information for specifying the section which is supposed to be an object as a sample object is stored so as to be related to the image.

Figure 23:
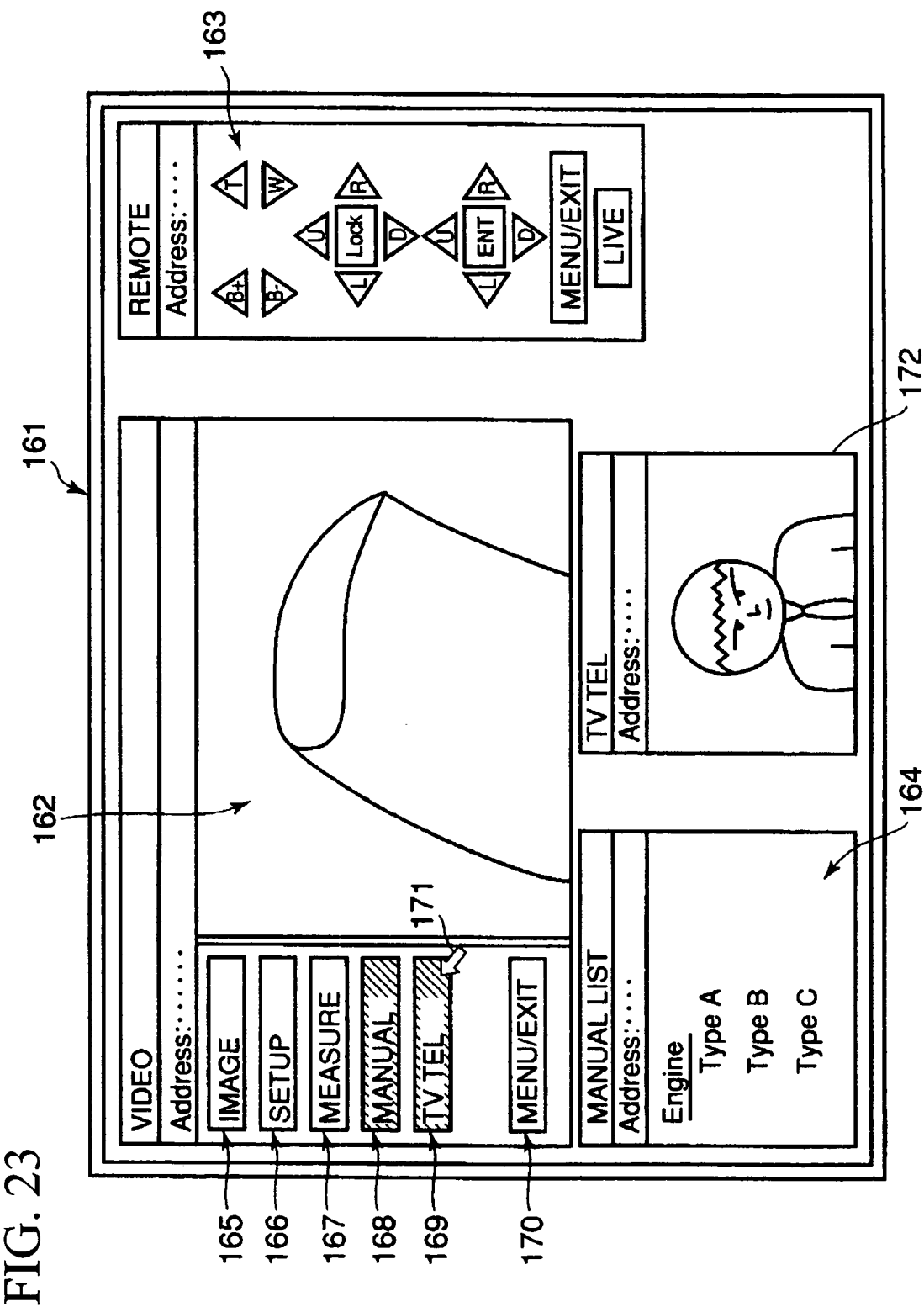
FIG. 23 is an example for a second manual instruction.

Next, an example is shown in FIG. 23 in which a TV telephone menu "TVTEL" is selected such that the person who performs the examination and operates the main remote control device 2 and the person who makes the decision communicate by images and voices with each other. The cursor 171 click the "TVTEL" so as to convert the display. In this browser display surface, the display for the examination manual and the camera image 172 are displayed together. In this example, the camera image 172 is displayed as a real time motion image in a central beneath of the display 161.

Figure 24:
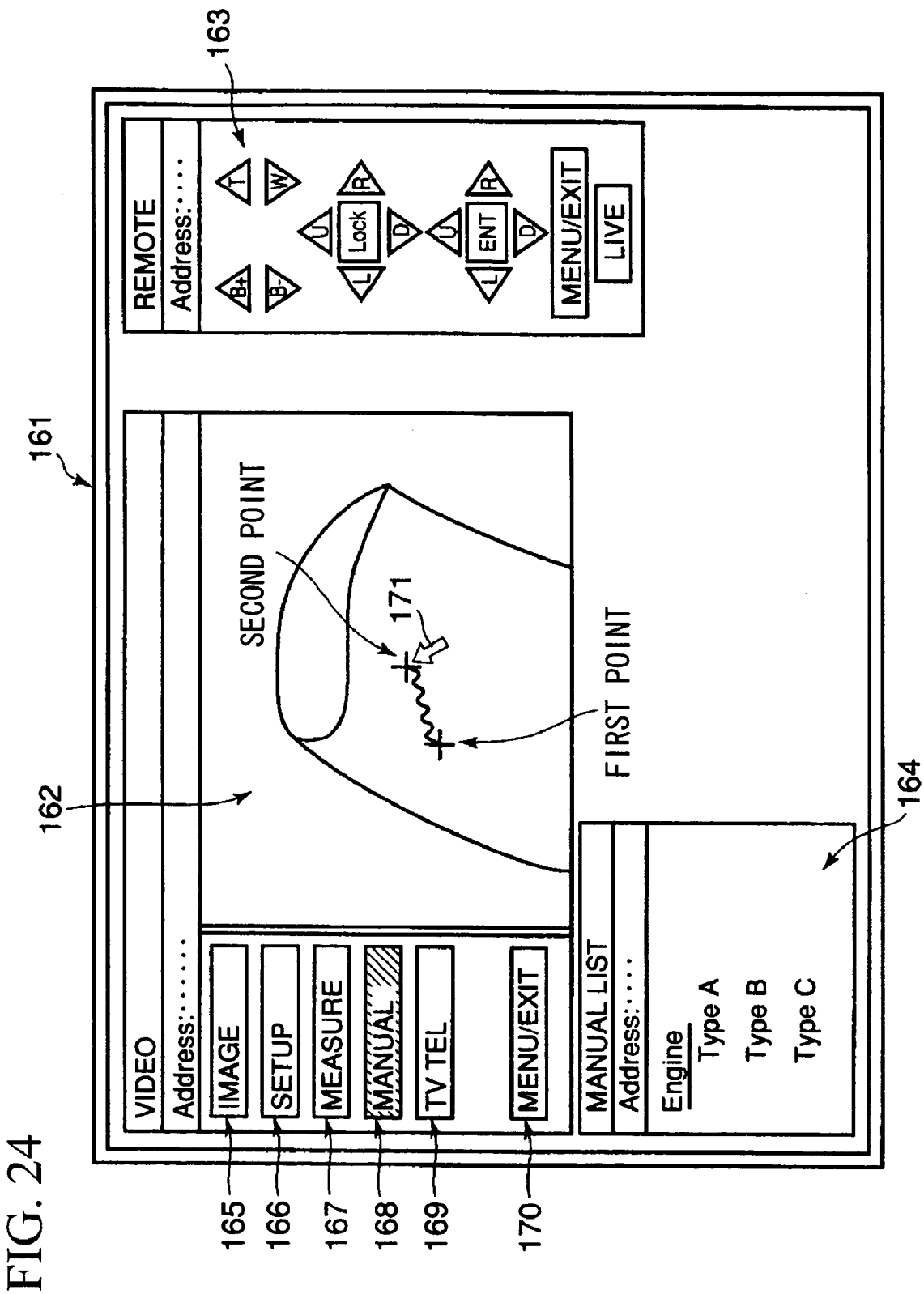
FIG. 24 is an example for a third manual instruction.
Figure 25:
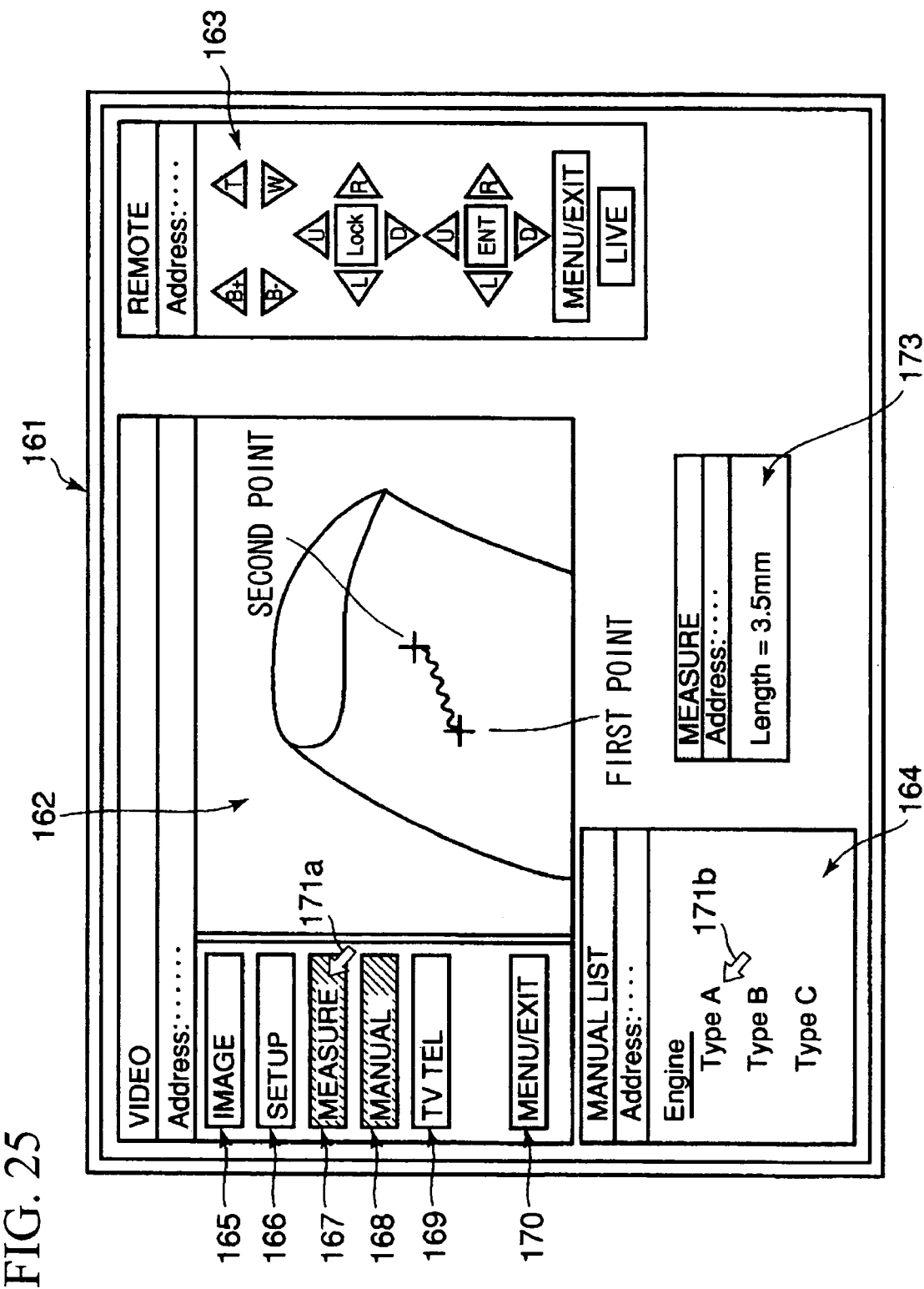
FIG. 25 is an example for a third manual instruction.

FIGS. 24 and 25 are view for display surfaces for explaining the measuring operation for the length of the flaw which is generated on the sample object.

Here, if the measurement program is installed in the endoscope device itself or in the image display remote control device itself, it is possible to perform the measurement operation in the endoscope device or the image display section in the main remote control device respectively. Such a measurement result is displayed in another browser. However, if the measurement program is not installed, it is possible to display the measurement result on the browser by measuring by a measurement server in the external terminal which is connected to the network and downloading and receiving the measurement result as a file which is described in a server language such as an HTML. Such a measurement result can be stored in the HD, the PC card, or the image recording server which is connected to the network by selecting the "RECORD" menu. Also, it is possible to change the GUI easily only by overwriting the file and storing the overwritten file because the GUI is stored in a file format which is described in a server language such as an HTML etc.

First, in the display shown in FIG. 24, a cursor 171 is disposed on an end of a flaw of the sample object. A first point (measurement start point) is designated by clicking there. Next, the cursor 171 is moved so as to be disposed on the other end of the flaw; thus, a second measurement point (measurement end point) is determined. After that, as shown in FIG. 25, the "MEASURE" is clicked by a cursor 171 so as to be determined. By such operations, a calculation for measurement is performed according to the preset program; thus, the measurement result for the length is displayed in a central beneath of the display surface. In this example, a length of the flaw is measured to be 3.5 mm.

As explained above, according to the first to the fourth embodiments and their modified embodiments, the endoscope device and the main remote control device are operated by a wireless communication. Therefore, it is possible to prevent conventional problems that the cables could not be handled desirably, the examination site could not move desirably, and the cable disturbs the persons' legs during the examination.

Also, if the person who performs the examination cannot determine whether or not the sample object indicates a desirable endoscope image, it is possible to transmit the endoscope image and corresponding information and obtain the desirable endoscope image by operating the endoscope device by a remote control operation by the person who makes decision by connecting to the external terminal via the network; thus, it is possible to determine whether or not the image is desirable quickly. Therefore, there is not a time loss in which it was necessary to accompany a person who makes decision conventionally, and it was necessary to restore the image in the remote place. Therefore, it is possible to determine whether or not it is necessary to repair or replace the sample object quickly. In a conventional case, the GUI was built in a program in the endoscope device; thus it was possible only to rewrite the program so as to change a menu which is used more frequently by the person who performs the examination to be more higher priority. In contrast, in the present embodiment, it is possible to realize such a program change.

Next, a remotely controllable endoscope control system according to a fifth embodiment of the present invention is explained.

In the above explained first to fourth embodiments, acceptability for the examination is performed by the person who performs the examination or by the person who makes decision in a remote place. In such a case, if it is determined to repair the part and the part should be replace, such a part is desired to be obtained immediately.

Figure 26:
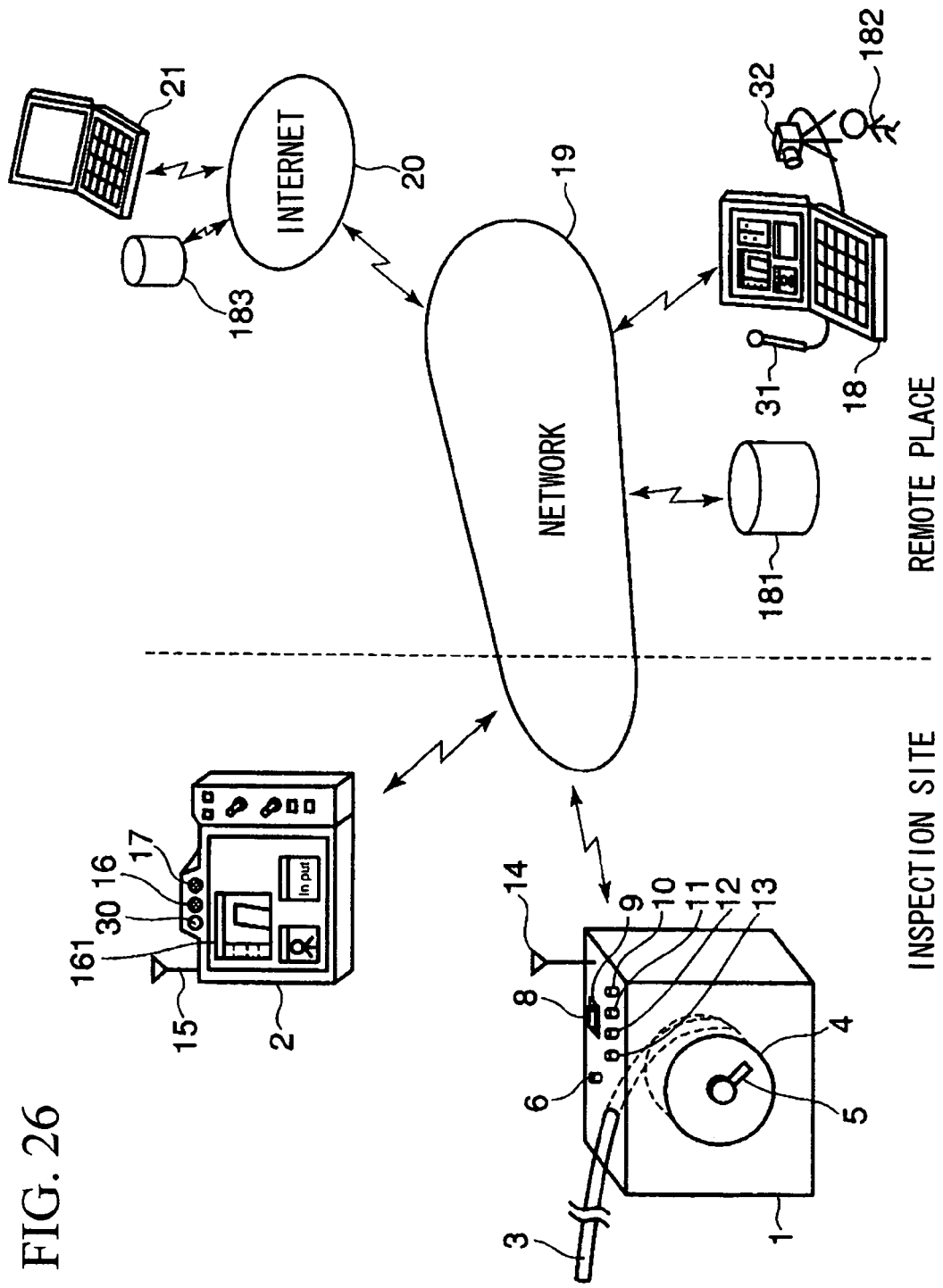
FIG. 26 is a view for a general structure of a endoscope control system according to a fifth embodiment of the present invention.

An information process center 181 which is disposed in a network for the endoscope control system which is explained with reference to FIG. 26 has a function for performing an image processing operation and a measuring operation for the above explained endoscope device. In addition, the information process center 181 has a function for arranging a distribution for the part which is necessary to be replaced. That is, it is possible to file an image record replay, an image processing operation (such as an adjustment for brightness and a trimming processing operation), and a measurement processing operation by using the received endoscope image and the information for specifying the section in the sample object. The information process center 181 can communicate with the endoscope device or the examination site by using a network such as a LAN and Internet, a mobile phone, and a PHS (personal handyphone system).

By doing this, the information process center 181 performs a measurement operation and a determining operation with reference to the endoscope image which is transmitted from the examination site via the network and the information which specifies a specific part in the sample object by using a person who performs such operations in the information process center. If a intolerable fault section is found such that it is determined to "repair" or "replace" the part, the distribution for the replacement part is performed. Also, if the person who performs the processing operation (in the information process center) cannot determine the degree for the fault and how to deal with the fault, the person who performs the processing operation can transmit the image and the corresponding information so as to ask the person 182 who makes the decision in the remote place for determining the degree of the fault and how to deal with the fault.

Figure 27:
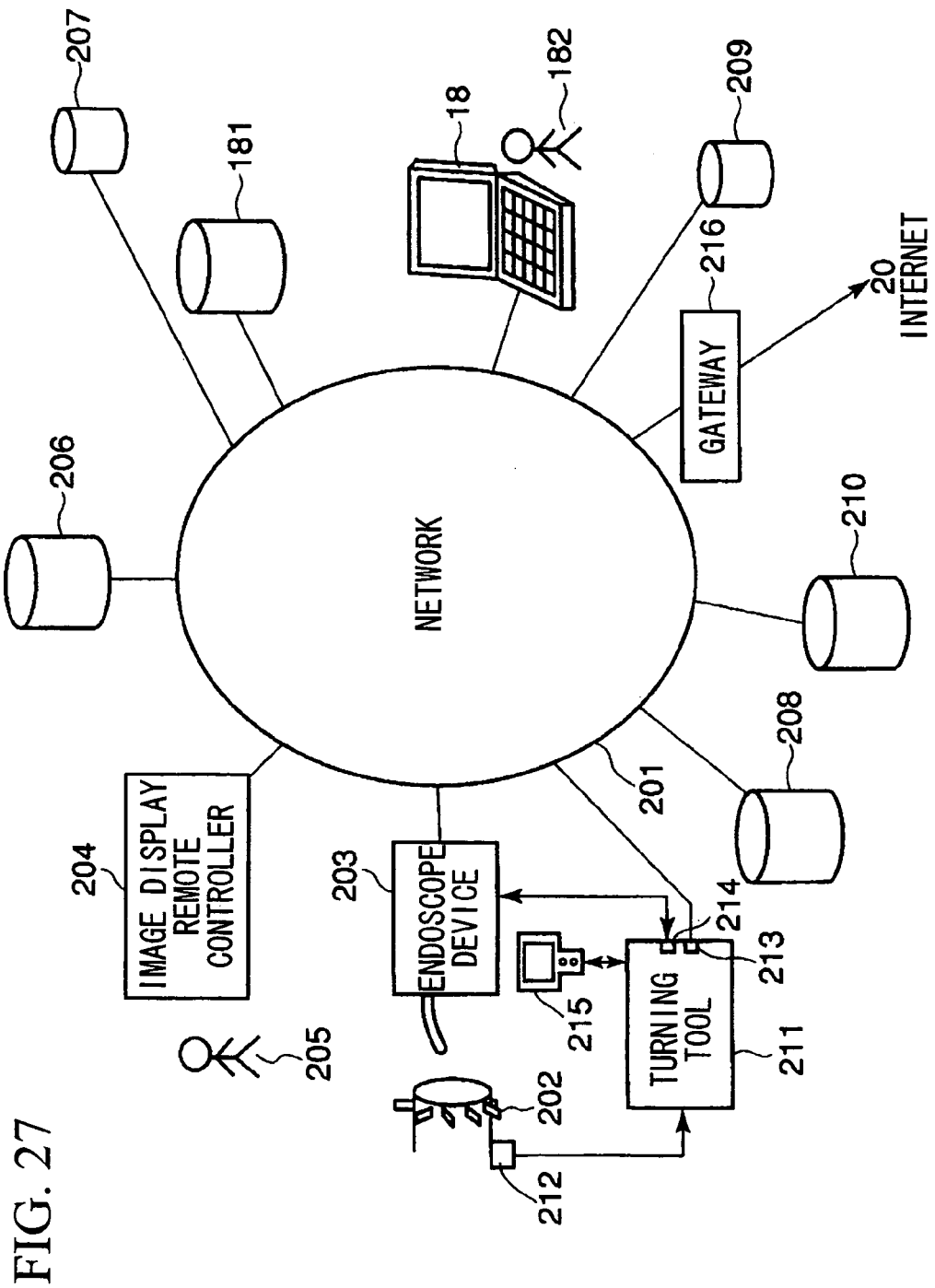
FIG. 27 is a view for an example of a structure according to the fifth embodiment.

In a specific example shown in FIG. 27, an endoscope device 203 for capturing the endoscope image for the sample object 202, an image display remote control device 204, a person who performs the examination for the endoscope device 203, an external terminal 18, a person 182 who makes decision for operating the external terminal 18, an instruction manual server 206, an endoscope repair center 207 for distributing the replacement parts for the endoscope, a sample object repair center 208 for distributing the members which form the sample object, a mail server 209, a data server 210, and a gateway 216 for connecting to the internet are provided.

First, a list for the members for forming the sample object which are stored in advance is read in the endoscope system for a preparatory stage for a case in which a measurement operation is performed by an endoscope system (the endoscope device 1 and the main remote control device 2) in the examination site. Alternatively, such a list is obtained by downloading from the data server 210 so as to spread.

In these spreading operation, an instruction manual data are downloaded by accessing the server in which an instruction manual for the sample object is contained from the "MANUAL LIST" in the "MANUAL" menu as explained above such that a display for selecting the list for the sample object such as a turbine for the engine is displayed. Such a display is used for specifying the members which are displayed in the endoscope image. For example, a turning tool 211 is connected to a gear box 212 in an engine as a sample object such that a turning tool control program is downloaded so as to control the turning tool 211. Here, the turning tool 211 is explained.

Turbine blades for the engine are disposed in the turbine in which the turbine rotate around a longitudinal direction in the engine. Also, a gear box 212 is disposed in the engine for adjusting the rotation such that it is possible to rotate the turbine by connecting an apparatus which is called as a turning tool 211 to the gear box 212 externally. The examination for the engine by combining the turning tool 211 and the endoscope device 203 is performed commonly.

Also, a button for operating the turning tool 211 is disposed in the turning tool 211 commonly. Also, it is possible to connect a remote controller 215 to the turning tool 211 commonly. It is possible to designate the turbine as a sample object among the type of the engine and the type of the turbine which are stored in the turning tool 211 by using these operation sections. Also, it is possible to designate the rotation speed for the turbine such that the turbine should rotated at the designated speed. Also, it is possible to control the rotation speed in a step manner in which a turbine is stopped for a certain period such as approximately ten seconds every time a blade is captured in a center of the endoscope image. If the rotation is controlled in such a step manner, it is possible to specify aggregated number of the blade since the examination for the turbine starts according to the rotation angle of the turbine and the number of the blades which are disposed on the turbine.

Also, a serial communication I/F section 214 for outputting the data for specifying the section to be examined in the sample object which are set in this manner and a network I/F section 213 are disposed in the turning tool 211. In addition, it is possible to connect the turning tool 211 to the endoscope device 203 and the external terminal (personal computer) via a communication port such as a serial port or a network I/F section.

A command which indicates various setting values is transmitted from the turning tool 211; therefore, the endoscope device and the external terminal deciphers the transmitted command. By doing this, it is possible to obtain the type of the engine and the type of the turbine. Additionally, it is possible to store the data which indicate the aggregated number of the blade so as to correspond to the endoscope image. Also, in contrast, it is possible to control the turning tool 211 by outputting the above explained various setting conditions and a stop command for the turbine to the turning tool 211 from the endoscope device and the external terminal.

In this way, it is possible to specify the corresponding member by using the control information and the information which is selected from the list for the members. In the list for the member, if the sample object indicates a jet engine, it is possible to specify the type of the engine and the aggregated number of the blades in the engine. Also, if the sample object is a pipe, it is possible to specify a position where the tip section of the insertion section exists by measuring a length of insertion from a tip of the pipe in the insertion section.

Also, it is possible to specify the current position of the tip of the insertion section in the pipe by obtaining a log path for the insertion path by disposing an acceleration sensor in the insertion section. In such a case, it is possible to obtain a serial number of the members as an object and d a product number by forming a three-dimensional image for forming member (3D image) for an inner structure (examination object space) of the sample object according to, for example, a design drawing for the sample object so as to clarify the members and sections for forming the sample object, combining the current position of the insertion section, the captured endoscope image, and the 3D image.

Consequently, if the person who performs the examination finds a fault such as a flaw in the endoscope image, the person who performs the examination operates the live button 46 in the main remote control device 2 as shown in FIG. 2 so as to switch from the motion image to the still image; thus, the image is fixed. As shown in FIGS. 18 and 19, the points (both ends) in the flaw are designated such that the stereo measurement (two-points measurement, depth measurement), or a comparative measurement is selected among the displayed measurement menu. The "MEASURE" 167 is executed so as to obtain the measurement result. Consequently, the information as a measurement result such as a measurement menu, an image in which points to be measured is inputted, and the information which specifies the sample object and the members which form the sample objects are transmitted to the information process center 181 via the network.

According to the measurement result, level for the default is determined by the person who performs the processing operation in the information process center 181. For such a result of the determination, there are "REPAIR NECESSARY", "NOT NECESSARY TO DEAL WITH", and "NECESSARY FOR DETERMINATION BY THE PERSON WHO MAKES DECISION", etc. If it is determined for "REPAIR NECESSARY", the information process center 181 orders a replacement part to the sample object repair center 208. The date for delivering the repair part is replied from the sample object repair center 208. The information process center 181 replies to the person who performs the examination for the value and the level of the fault, a method for how to deal with the fault, and the date in which the replacement part is supposed to be deliverd which are used for the de termination. If it is determined for "NOT NECESSARY TO DEAL WITH", the information process center 181 transmits the value which is used for the determination and the level of the fault to the person who performs the examination.

If it is determined for "NECESSARY FOR DETERMINATION BY THE PERSON WHO MAKES THE DECISION", the information process center 181 transmits the value which is used for the determination and the level of the fault together with the endoscope image etc. to the external terminal 18 so as to ask the person who makes the decision for determination. The person who makes decision makes decision according to the transmitted information. Also, it is possible to communicate with the examination site by the TV telephone if necessary. Also, it is possible to browser the recorded image by operating the endoscope device remotely by the person who makes decision and observe the point of fault by operating the endoscope actually. Consequently, the processing operation such as "NOT NECESSAEY TO DEAL WITH" or "REPAIR NECESSARY" is performed in the information process center 181 which receives the determination result from the person who makes the decision.

The information process center 181 makes a report for the image which includes the endoscope image, the measurement result, the value which is used for the determination, the level for the fault, a method for how to deal with the fault, and repair schedule so as to file. These can be browsed always via the network.

Here, explanations are made in the above embodiments for a case in which the information process center performs the determination. However, it is possible to perform the determination by installing the examination program in the endoscope system. Also, it is possible to order the repair part from the person who performs the examination to the repair center directly.

Presupposition for the above explained information process center 181 is that the person who performs the processing operation should stay in the information process center 181 on a regular basis. However, the present invention is not limited to such a presupposition. That is, it is possible to realize such operations automatically according to preset sequences. For example, it is possible to determine the acceptability of the image by measuring the image which is transmitted from the endoscope device 1 and the image for the sections to be examined automatically. For example, the acceptability for the image is determined by measuring the image which is transmitted from the endoscope device 1 and the image for the sections to be examined in the sample object automatically such that the determined result is replied/transmitted to the examination site or the external terminal of the person who makes decision by an e-mail etc. If it is determined for "REPAIR NECESSARY", a processing operation for ordering the replacement part to the sample objection repair center 28 is executed.

In addition to the above explained services which are performed by the centers and the servers, the information process center 181 performs various services such as a "3D image display service" in which a wire frame is displayed according to the 3D information which is obtained from the stereo adapter, an "optimum AD selection" in which an optimum optical adapter is selected by determining the image-capturing conditions such as an optimum perspective angle and depth of field if the sample object is selected from the list, a "Report production service" in which a report which is produced by the HTML and the DOC if the image file is transmitted which includes a printing operation and delivering operation, a "Q and A collection browsing service" for browsing the Q and A collection regarding a method for using the endoscope, and a "Service for introduction for former cases" in which former cases for using the endoscope can be retrieved and browsed. Here, in a conventional case, it was possible to see the documents for the sample object and the instruction manual only by storing these documents in media or bringing these documents to the examination site. In contrast, in the present invention, it is possible to obtain these documents via the network easily so as to display.

Also, services such as a "remote maintenance service" in which a repairing operation for the endoscope is automated, and a "status for repairing operation notifying service" in which the current status of the repairing operation for the endoscope is retrieved are provided in the endoscope repair center. Furthermore, a "downloading service" in which a latest program for the endoscope such as a maintenance manual and drawings for the sample object is downloaded is provided.

As explained above, according to the present embodiment, it is possible to realize a quicker repairing operation because the endoscope image is captured so as to transmit the corresponding information to the information process center via the network such that the determination for the acceptability of the sample objects and the ordering operation for the replacement part are performed. Also, it is possible to ask the person who makes decision for her or his determination; thus, it is possible to realize more adequate operation for the sample object.

Explanations have been made so far with regards to the above embodiments. In addition, more importantly, the English Specification of the present patent application includes inventions below.

(1). An endoscope device comprising:
    a network server device which stores a graphical user interface (GUI) as an image information which is written in a server language; and
    a network interface (network I/F).
(2) An endoscope device further comprising:
    an image display section; a network I/F device;
    a WWW browser device; and
    an operation device for operating the endoscope device.
(3) An endoscope device according to the above item (2) wherein the operation device for the above endoscope device is a remote control device.
(4) An endoscope device according to the above item (2) wherein the operation device for the above endoscope device is a touch panel.
(5) The remote control device according to the above item (3) is a separate member from the image display section.
(6) An endoscope device according to the above item (2) is provided with a wireless communication device.
(7) An endoscope device according to the above item (6) is a remote control device which is provided with a wireless communication device.
(8) A network endoscope system which is provided with a control device for controlling the endoscope device which is connected to the endoscope device via the network.
(9) The remote control device according to the above item (8) is an image display remote control device which is provided with an image display device, a network I/F device, a WWW browser device, and an operation device for operating the endoscope device.
(10) The control device according to the above item (8) is a separated member such as a remote control device from the image display device such that the control device is provided with a wireless communication device for controlling the endoscope device.
(11) The remote control device according to the above item (8) is an image display remote control device which is provided with an image display device, a network I/F device, a WWW browser device, and an operation device for operating the endoscope device.
(12) The image display remote control device according to the above item (11) is provided with an image capturing device, a voice inputting device, and a voice replaying device.
(13) The personal computer according to the above item (11) is provided with an image capturing device, a voice inputting device, and a voice replaying device.
(14) The network I/F device according to the above item (1) is a wireless LAN or an Ethernet.

(15) The network server device according to the above item (1) is a Web server, a motion image distributing server, a file transmitting server, or a PPP server.
(16) The server according to the above item (15) is a Web server having an HTTP protocol, a file transmitting server having an FTP (File Transfer Protocol), a mail transmitting server having an SMTP (Simple Mail Transfer Protocol), a mail receiving server having a POP (Post Office Protocol).
(17) An endoscope device according to the above item (1) is provided with an external image outputting device.
(18) An endoscope device according to the above item (1) is provided with an external image inputting device.
(19) An endoscope device according to the above item (1) is provided with an external voice outputting device.
(20) An endoscope device according to the above item (1) is provided with an external voice inputting device.
(21) An endoscope device according to the above item (1) is provided with a remote controller connecting section.
(22) An endoscope control system for communicating the image information by connecting to the network for the communication comprising: a network server device which is provided with an interface for executing an external application software and stores a graphical user interface (GUI) which is a display information which is written in at least a server language and external application software; and a network interface (network I/F). In this item, more specifically, the external application software corresponds to a CGI file and ASP file. The interfaces for establishing and executing the program and a script in these CHI file and the ASP file are CGI and ASP.

Figure 28:
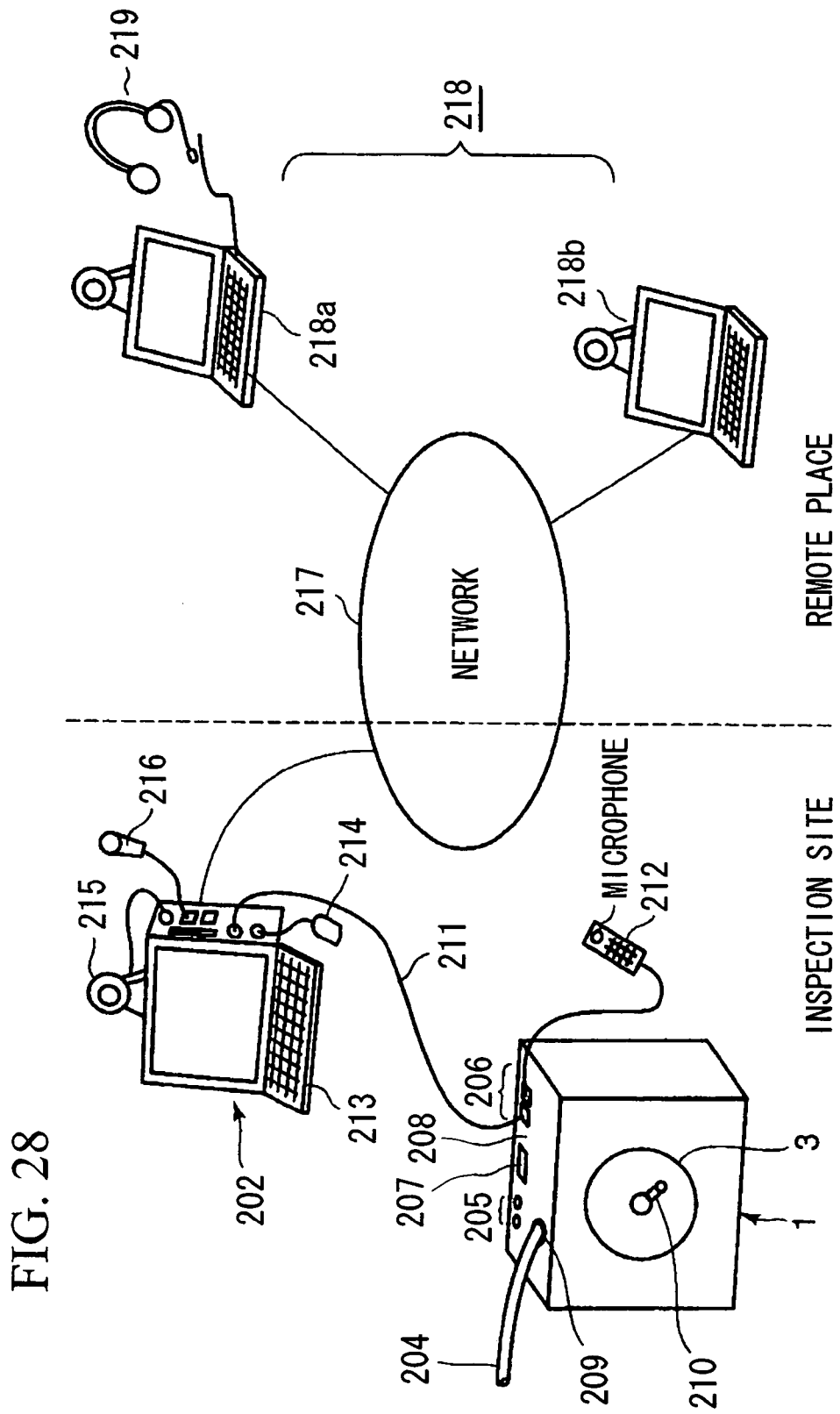
FIG. 28 is a view for a general structure of a remote controllable endoscope control system according to a sixth embodiment of the present invention.

FIG. 28 is a view for a general structure of a remote controllable endoscope control system according to a sixth embodiment of the present invention. In embodiments below in the endoscope control system according to the present invention, explanations are made for a case in which the above explained endoscope device main body and a peripheral sections are contained unitarily in a frame so as to be movable. However, the present invention is not limited to such a structure. A structure in which the endoscope device and peripheral sections are separable can be used for a communication system according to the present invention.

The endoscope system comprises an endoscope device 201 which is used mainly for an industrial purpose and a control section 202 which is formed by a personal computer etc. so as to perform a transmitting/receiving operation for an image (endoscope image), a voice, and a control signal by an electric signal or an optical signal by the endoscope device 201 and a cable so as to control the endoscope device 1 and the communication operation with the external terminal.

A long insertion section 4 which is wound by a rotative drum 203 is contained in the endoscope device 201. Various switches 205 including a power supply switch, various connectors 206 for performing an inputting/outputting operation with external apparatuses, an operation panel 208 to which a memory card slot 207 is disposed for attaching/detaching a detachable recording medium such as a PC card, and an insertion section mouth 209 from which the insertion section 205 protrudes and winding therefore are provided on an upper surface of a main body of the endoscope device. Also, a handle 210 for winding the drum is disposed on a front end of the main body of the endoscope device. Also, it is acceptable if a motor for winding the drum is disposed so as to wind the drum electrically.

The above various connectors 206 is provided with a connector to which a terminal a built-in microphone remote control switch (hereinafter called a remote controller) 212 engages and various connectors for other purposes.

Also, in the control section 202, a keyboard section 213 and a mice 214 for performing inputting operations, an image capture 215 for capturing an expression on a face of the person who operates the control section 202, a microphone 126 are connected to a network 217 such as a LAN by a cable via an external connecting terminal. It is acceptable if a communication may be performed with a network by an optical signal in such a cable as long as the cable is used not only for the electrical signal but also n optical signal by a communication interface. Here, it is acceptable if an inputting operation may be performed by disposing a touch panel on a display surface in place of a keyboard or a mice.

At least an external terminal 218 can be connected to such a network 217. Here, an example is shown in which two external terminals 218a and 218b are connected. Here, these external terminals 218 are provided with an inputting device which is similar to those in the control section 2, a display device, a processing operation device, and a processing program for a remote control. An example is shown for such an external terminals 218 in which a headphone 219 which has a built-in microphone is used.

Figure 29:
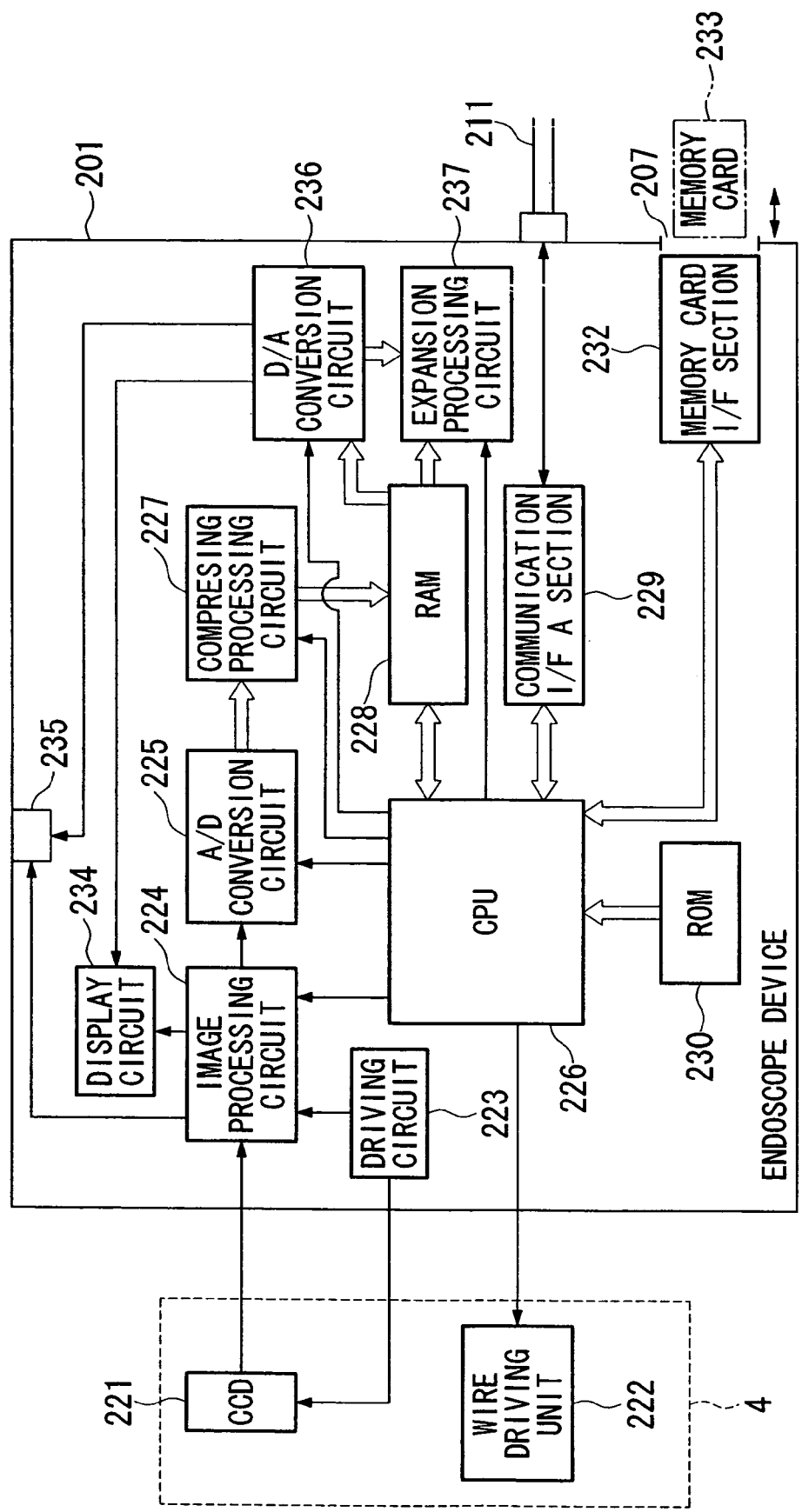
FIG. 29 is a block diagram for an endoscope image processing operation and a communicating operation in an endoscope device according to the sixth embodiment of the present invention.

In FIG. 29, a block diagram for showing an endoscope image processing operation and a communication operation in the endoscope device 1. Here, the structure and operation therefore are explained. Here, explanations are made for the present invention by showing only necessary members and sections. It should be understood that necessary members and sections for performing ordinary functions are already disposed.

An image capturing element (such as CCD) is provided on a tip section of the insertion section 204 which is used in the endoscope device 201. The tip section can be bent freely by operating a plurality of operation wires which are connected to the tip section (not shown in the drawing) by a wire driving unit 222. Thus, it is possible to obtain a wide range of the endoscope image from the CCD 221.

The CCD 221 is driven by a driving circuit 223 in the endoscope device 1 so as to transmit an image (endoscope image) signal which is converted into an electric signal by performing an optical-electric converting operation to an image process circuit 224 successively. The image process circuit 224 performs various image processing operations such as an amplification and a chromatic separation according to a timing signal from the driving circuit 223. Also, it is possible to output the output from the image process circuit 224 to an image external terminal 235 and a display circuit 234. The display circuit 224 can display the inputted image.

Next, a digitizing operation for the image signal is performed by an A/D conversion circuit 225 so as to output to the compressing process circuit 227 in image data condition. The compressing process circuit 227 performs a compressing operation according to an appropriate compressing method for the image data (still image and motion image) in which an orthogonal conversion code is converted into a variable length code according to a DCT (discrer cosine transform) method. Such compressed image data are stored in the RAM 228 successively. During such an image processing operation, it is possible to perform various image adjustment/processing operation such as an adjustment for Brightness and a trimming process operation to the image data (endoscope image).

After the compressed image which is stored in the RAM 228 is extended in a expansion process circuit 237, it is possible to convert the expanded image into an analogue signal by a D/A conversion circuit 236 so as to output to the image external terminal 235 and the display circuit 234. It is possible to convert a a non-compressed image which is stored in the RAM 228 into an analogue signal by a D/A conversion circuit 236 so as to output to the image external terminal 235 and the display circuit 234.

These circuit and the unit are driven by a CPU 226 which is formed by a micro computer etc. controllably. The CPU 226 reads out the processing program which is stored in the ROM 230 in advance so as to spread and operate according to a control sequence based on the processing program. Here, the RAM 228 is used for storing the compressed image data. It is acceptable if the RAM 228 is used for serving a working area for spreading the processing program for the ROM 230. Also, it is acceptable if the RAM 228 serves for a function for storing the information which relates to the communication.

Furthermore, the data are transmitted in such a way that the stored image data are read out from the RAM 228 by the CPU 226 so as to be transmitted to the control section 202 from a communication interface (I/F) such as a communication I/F section A229 which uses a USB interface through a cable 211 (electric wire or an optical fiber cable) in an electric signal manner or an optical signal manner.

Furthermore, the endoscope device 201 is provided with a memory card I/F section 232 for storing the image information which include the image data in a memory card 233 so as to store in a memory card 233 which is attached to a memory card slot 207 which is disposed on a main body of the device. Also, it is possible to form these circuit and the CPU etc. in an integrated manner such as a one-tip micro computer manner. If a television method is used in the above case, the above processing operation is repeated by every ⅓₀ seconds if the frame frequency is indicated by NTSC method. The above processing operation is repeated by every ½₅ seconds if the frame frequency is indicated by PAL method.

Figure 30:
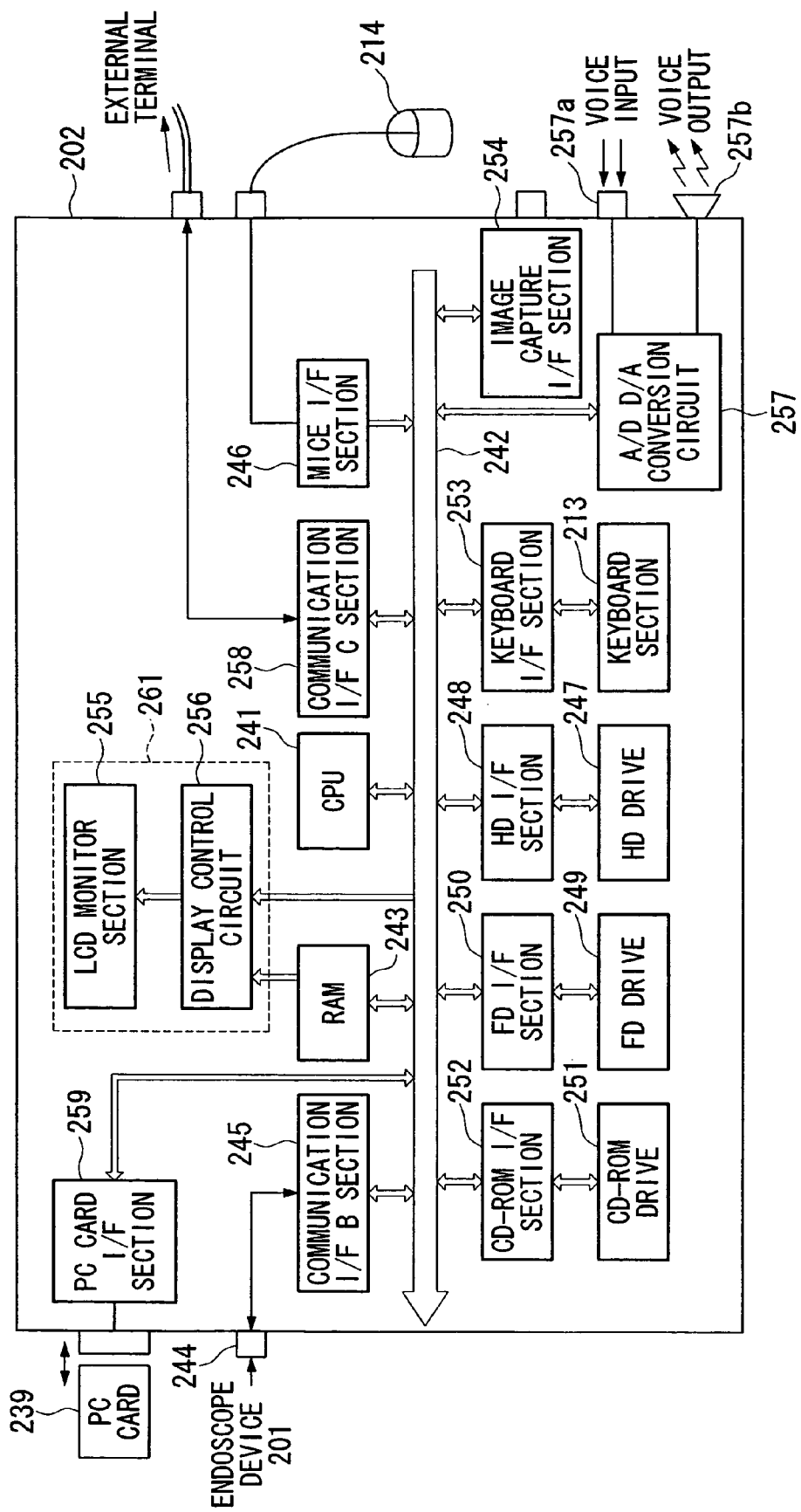
FIG. 30 is a block diagram for a control section according to the sixth embodiment of the present invention.

A block diagram for the control section 202 is shown in FIG. 30. Explanations for the structure is made as follows. Here, explanations are made for the present invention by showing only necessary members and sections. It should be understood that necessary members and sections for performing ordinary functions are already disposed.

In the control section 202, the members which forms the control section 202 transmit/receive the signal and data via an internal bus 42 as explained later.

In addition, a CPU 241 which is formed by a micro computer etc. for controlling an entire control section 202, a RAM 243 which spreads the processing program and serves for a working area for the CPU 241 so as to be able to store the image data (endoscope image) which are transmitted from the endoscope device 1, a communication I/F section 245 which performs a communication operations for the information which include the image data from the endoscope device 201 via the cable 211 and the external terminal 244 shown in FIG. 29, a mice I/F section 246 which is connected to a mice 214 via the external terminal, a communication I/F section 258 which performs a communication operation with a plurality of external terminals 218 via the network which is explained later, and a keyboard I/F section 253 which transmits the input signal which is inputted from the keyboard section 213 to the CPU 241 are connected to an internal bus 242.

Also, a hard disk (HD) drive 247 in which various processing programs are contained, a detachable flexible disk (FD) 249 such as a floppy (registered trademark), and a CD-ROM drive 251 are connected to the inner bus 242 via each interface section (HD I/F section 248, FD I/F section 250, CD-ROM I/F section 252).

Furthermore, a display control circuit 256 which controls the display operation in a LCD monitor section 255 for displaying various information such as image data which are read out from the RAM 243, a PC card I/F section 259, an image capture I/F section 254, and an A/D·D/A conversion circuit 257 are connected to the internal bus 42. The PC card I/F section 259 serves such that the PC card (SRAM, flash memory, etc.) 239 should store the information which include the image data (endoscope image) from the endoscope device 201.

Also, the image capture I/F section 254 performs a compressing process operation for performing a communication and transmission for the image data from the image capture 215. Such compressed image data are transmitted to the network 217 via the communication I/F section C258 from a motion image distributing server which is not shown in drawing. Alternatively the compressed image data are transmitted to the HD drive 247 so as to be stored there, or displayed in the LCD monitor section 255.

Also, the A/D·D/A conversion circuit 257 performs an A/D conversion operation for the voice signal which is inputted from the microphone 216 etc so as to generate a digital voice signal. The generated digital voice signal is transmitted to the network via a communication I/F section C258 together with the captured image data or stored in the HD drive 247. Furthermore, a D/A conversion operation is performed to the voice data which are read out from the HD drive 247 or received from the network 217; thus, the converted voice data are emitted from a speaker which is not shown in drawing in a voice condition.

In the control section 202 which is formed in this way, the CPU 241 spreads the processing program which is built in the HD drive 247 in a predetermined area in the RAM 243 so as to instruct a processing operation according to a control sequence according to the spread program. Also, a restoring process operation is performed for the image data of the endoscope device 201 which are downloaded via the communication I/F section B245 and the image data which are read out from the RAM 243 such that the compressed image data are restored to be an initial condition. Furthermore, the restored image data are converted into an image signal in the display control circuit 256 so as to be displayed in the LCD monitor section 255.

Figure 31:
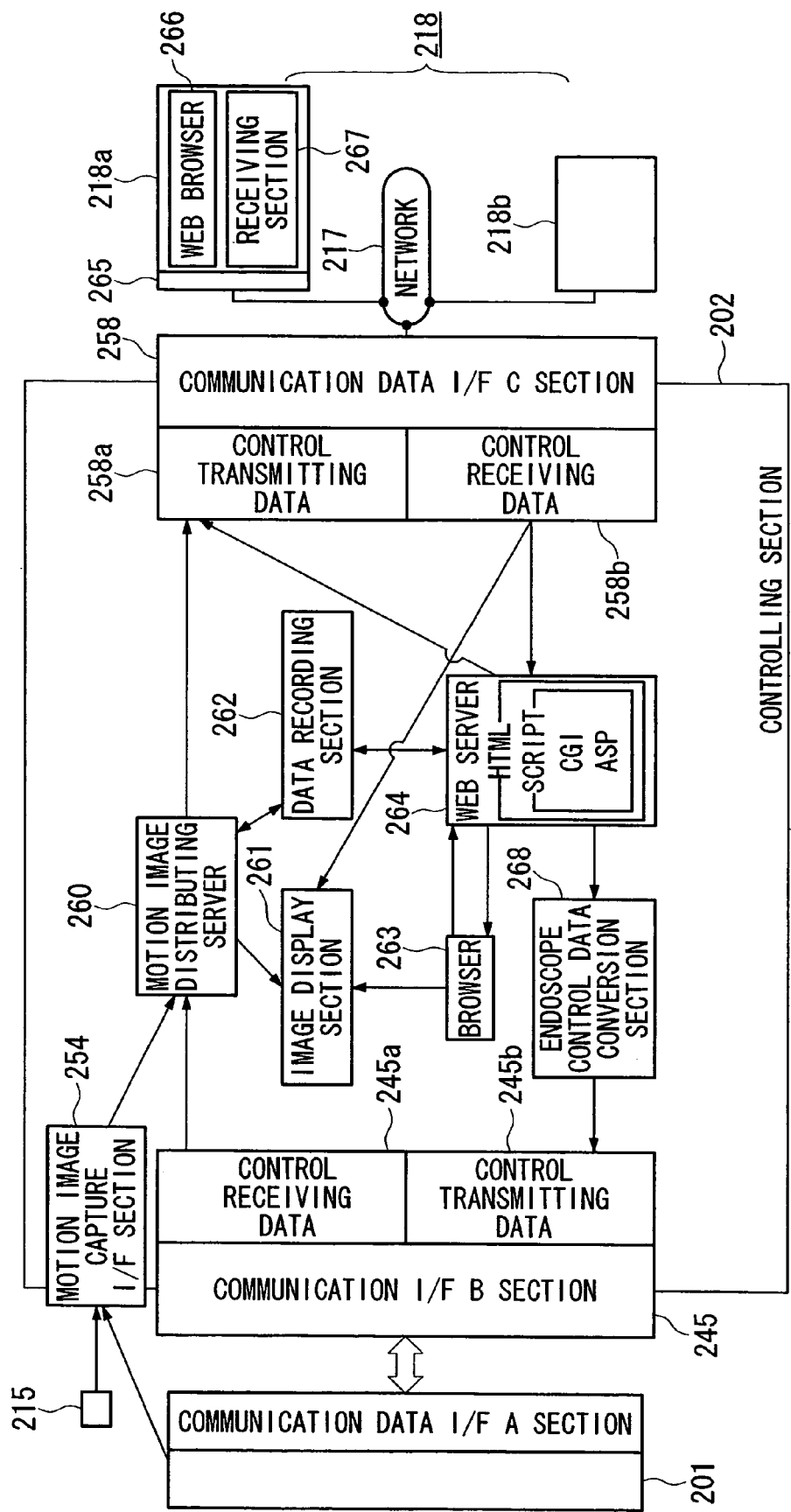
FIG. 31 is an example for a communication function of the endoscope control system.

Next, an example for a communication function in the endoscope control system according to the present embodiment is shown in FIG. 31. Explanations for the communication function are made with reference to a structure of the device which is shown in FIGS. 29 and 30.

In this system, the endoscope device 201 is provided with a communication I/F section A229 which performs a communication operation for the information which includes the image data (endoscope image) by using, for example, a USB interface method.

The control section 202 is provided with a communication I/F section B245 which performs a communication operation with the communication I/F section A229. The communication I/F section B245 includes a received data control section 245a and a transmitting data control section 245b. Also, an image capture I/F section 254 performs a compressing processing operation for the motion image so as to upload the compressed motion image to the motion image distributing server 260. Also, it is accepatable if the image capture I;F section 254 is connected to the endoscope device 201 via a cable so as to obtain a motion image to which an image processing operation is performed.

The motion image distributing server 260 image data which are from the motion capture I/F section 254 and the received data control section 245a to a transmitting data control section 258C for the image display section 261 and the communication I/F section C258. The image display section 261 is formed by the above explained LCD monitor section 255 and the display control section 256.

Also, a WWW (Web) server 264 which performs a communication operation for the image which are described in, for example, an HTML (Hyper Text Markup Language) by the HTTP (Hype Text Transfer Protocol) is disposed in the control section 202. An ASP (Active Server Page) and a CGI (Common Gateway Interface) which output the HTML by establishing programs from the Web page and the Web server which are described in the HTML format are included in the Web server 264.

Consequently, the information from the Web server 264 and the image data from the motion image distributing server 260 are transmitted at least the external terminals 218 (218a, 218b) which are connected to the network which is formed by a LAN etc. according to a packet communication method etc. via a transmitting data control section 258C. A communication I/F section D265, a Web browser 266, and a receiving section 267 are disposed in the external terminal 218 such that the image data (endoscope image and image of the person who operates the device) are received by the receiving section 267 through the communication I/F section D265. Here, the person (supervisor) who makes the decision observes the endoscope image by the external terminal 218. Also, the endoscope control data converting section 268 converts the signal to a driving control signal for the endoscope device 201 by using the HTML and the script which relates to the driving control operation for the endoscope device in the Web server through the external terminal 218 and the control section 202; thus, the signal is transmitted to the transmitting data control 245b.

The endoscope image and the information in such image, and image which resembles various switches which are provided in the remote control device 212 for performing a remote control operation for the endoscope device 201 which is explained later are displayed on a display surface of the external terminal 218. If the switch display section for the remote control device which is displayed in an image manner is designated (clicked) by an inputting device such as a mice, it is possible to perform a remote operation. It is certainly acceptable if a touch panel is disposed on a display surface of the external terminal so as to input data by pressing the touch panel by a finger tip.

Also, instruction signals from the external terminal 218 are transmitted to the Web server 264 via a received data control section 258b in the communication I/F section C258 in the control section 202 through the Web browser 266. Consequently, the received instruction signal etc. is converted into an appropriate control signal by the endoscope control data converting section 268 so as to be transmitted to the endoscope device 201 through the transmitting data control section 245b. The endoscope device 201 is operated according to the received control signal. For example, if the instruction indicates for bending the tip section of the insertion section 4 toward a certain direction, the tip section of the insertion section 4 is bent accordingly. If such a operation is performed, a signal which indicates that such an operation is completed or that the operation is erroneous is transmitted to the external terminal 218 so as to let the person who makes decision know by displaying the signal on a display etc. of the external terminal 218.

Here, authentication for the remote control operation for the endoscope device 201 by the external terminal 218 in the present invention is entitled by a switching operation by the person who performs the operation or by a control section 202 according to a preset program. Also, if a plurality of external terminals are connected to the network, it is acceptable if the request from the person who makes decision may be determined selectively by the person who performs the operation. Also, it is acceptable if a priority is added to the external terminals in advance. Also, it is acceptable if the operation is performed according to the requested order.

Figure 32:
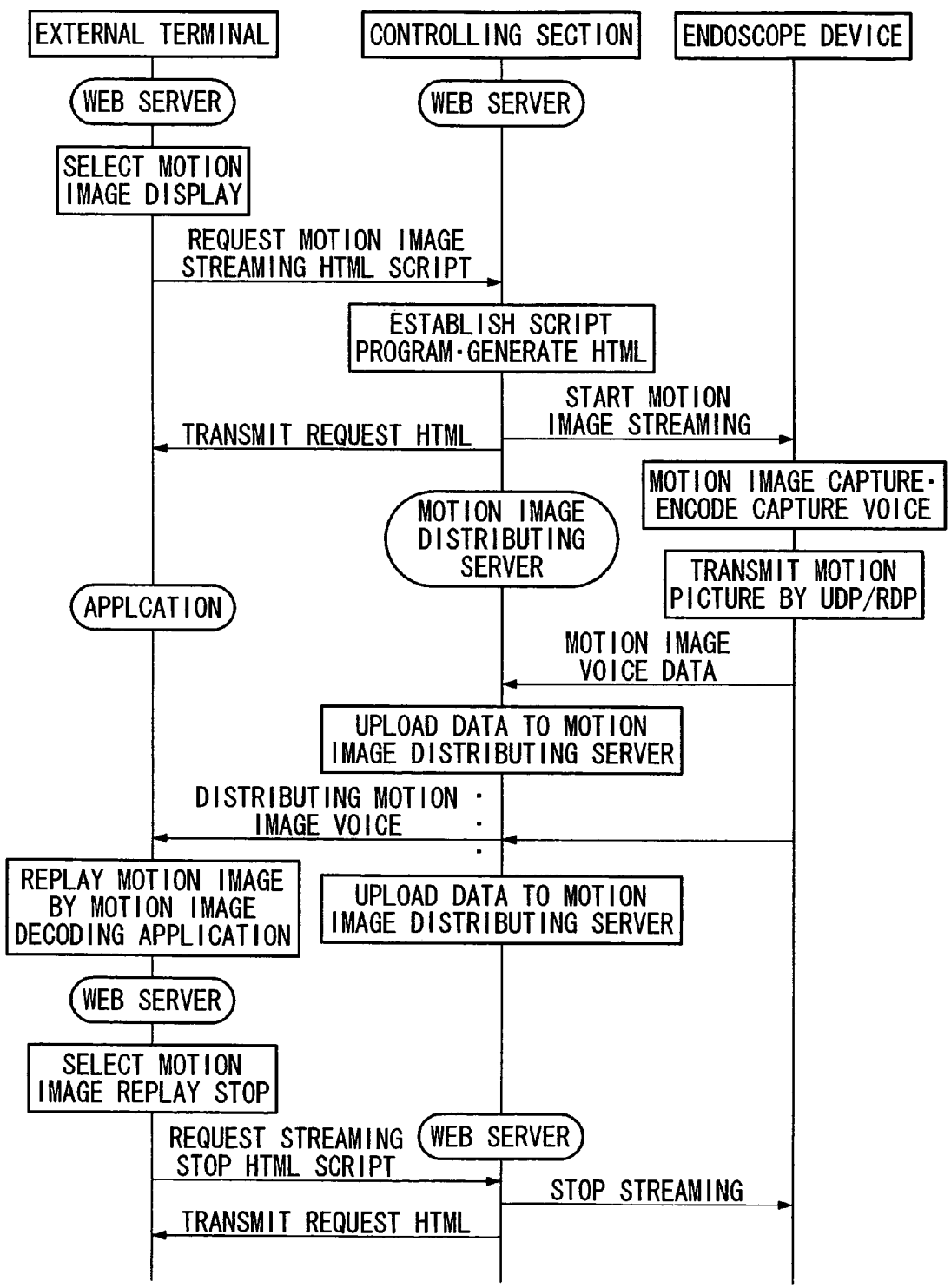
FIG. 32 is a timing chart for explaining a distributing operation for a motion picture between the external terminal and the control section in a network in an endoscope control system.

Next, explanations are made for a distribution of the motion image between the control section and the external terminal which uses the network in the endoscope control system according to the present embodiment with reference to a timing chart shown in FIG. 32.

The endoscope device 201 inserts the insertion section 204 into the sample object so as to obtain an image for a section which faces the tip section of the insertion section 204. In this case, it is a presupposition that the person who performs the operation asks the person who makes decision in a remote place for the acceptability of the captured section in the endoscope image.

As similarly as explained above, the person who makes decision accesses the Web server in the control section 202 via the network which is formed by the Web browser for the external terminal 218 which is owned by the person who makes decision; thus, the reference to an ID and a password is performed. After that, the connection is allowed. Consequently, after a mutual communication is enabled, a switch image (HTML) in which switches for instructing a similar operation similar to that of the remote control device 221 such as at least an image (still image or motion image) which is captured by the CCD 221 in the insertion section 204, information (HTML) which relate to the image, and an image processing instruction for the zooming timing for the image are displayed on a display of the external terminal 218 as a browser display. The switch image may be disposed in a similar manner for the switch disposition for the remote control device 212. Also, it is acceptable if a user may customize the disposition freely.

First, the person who makes decision instructs to select the motion image on the switch image (HTML) which is displayed on the browser. A motion image streaming HTML script request is performed by this instruction to the control section 202. According to this request, the control section 202 establishes a script program so as to convert to a signal for driving the endoscope device 201 and instruct to start the streaming operation for the motion image to the endoscope device 201. According to this instruction, the endoscope device 201 starts the motion image streaming operation such that the motion image (image capture) in which the CCD 221 is captured and a voice (voice capture) are encoded.

Consequently, the image data (including voice data) are transmitted to the control section 202 according to a UDP/RTP. Also, in such a case, the control section 202 transmits the HTML which is generated according to the request to the external terminal 218. The external terminal 218 receives this HTML so as to establish the motion image display application software. Also, it is acceptable if it is displayed on the browser.

Consequently, when the control section 202 receives the motion image and the voice data from the endoscope device 201, the control section 202 uploads the received data to the motion image distributing server 260 successively. The motion image distributing server 260 distributes the motion image to the designated external terminal 218. Such distributed latest motion image and the voice are transmitted to the external terminal 218 such that the distributed motion image and the voice are replayed on a motion image decoding application or the browser display.

Consequently, the person who makes decision instructs the external terminal 218 to select a stop for the motion image on a switch image (HTML) which is displayed on the browser. After that, the control section 202 establishes the script program so as to convert into the signal for driving the endoscope device 201 and instructs the endoscope device 201 to stop the motion image streaming operation. Simultaneously, the control section 202 transmits the HTML which is generated by the request to the external terminal 218. The endoscope device 201 stops transmitting the motion image to the control section 202.

Figure 33:
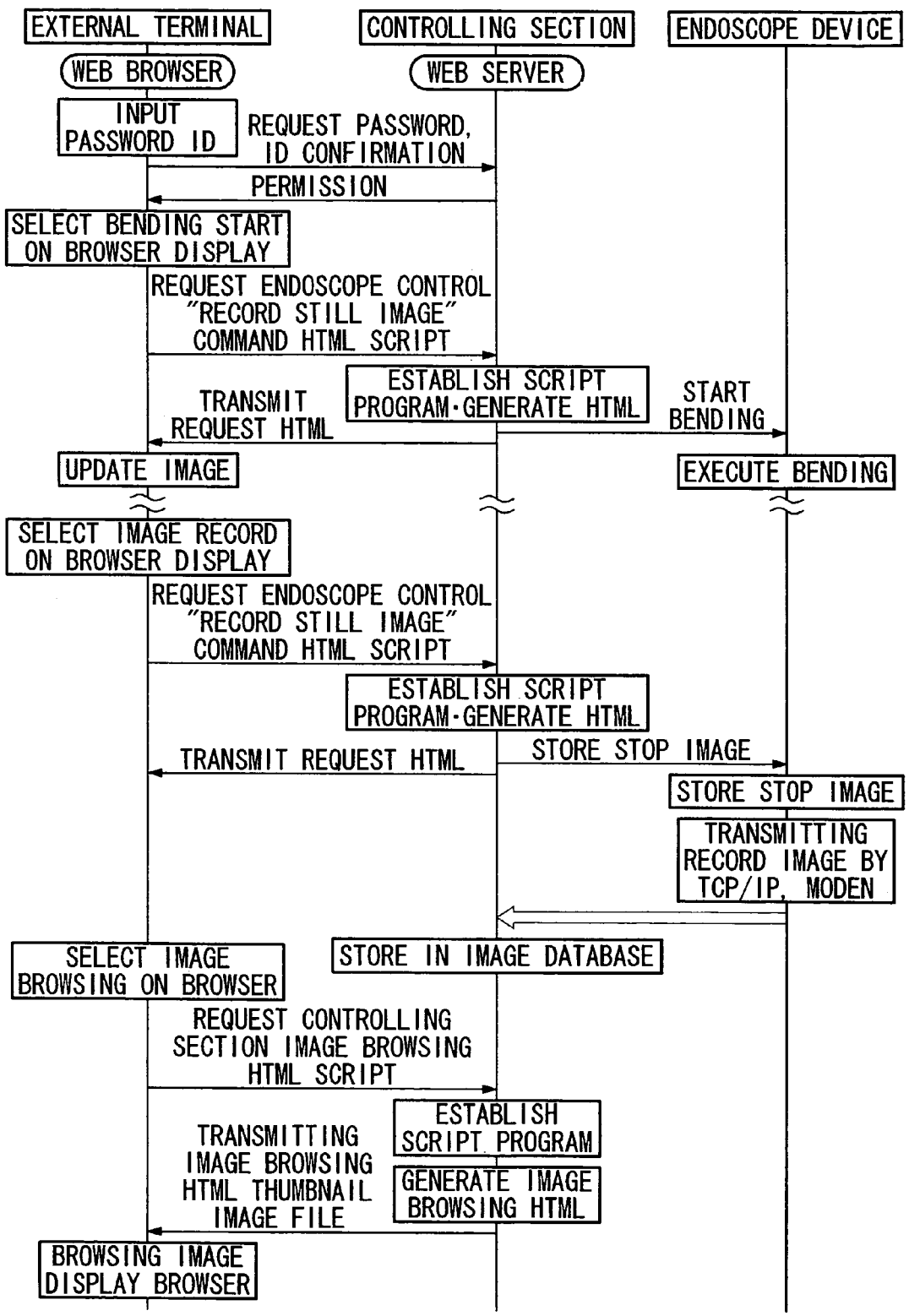
FIG. 33 is a timing chart for explaining a distributing operation for browsing image and a controlling operation for the browsing image between the external terminal and the control section in a network in an endoscope control system.

Next, explanations are made for operations for browsing and distributing an image and its control operation between the control section and the external terminal which uses the network in the endoscope control system according to the present embodiment with reference to a timing chart shown in FIG. 33.

Such a system can perform an image data communication by using a network such as a LAN and Internet etc. The endoscope device 201 inserts the insertion section 204 into the sample object so as to obtain an image for a section which faces the tip section of the insertion section 204. In this case, it is a presupposition that the person who performs the operation asks the person who makes decision in a remote place for the acceptability of the captured section in the endoscope image.

First, the person who makes decision accesses to the Web server in the control section 202 from the Web server in the external terminal 218 via a network. In such a case, an identification number (ID) and a password are formed so as to be selected; thus, an access from a third party is eliminated. It is certain that other selecting method can be used such as a selecting method which uses a hardware. Consequently, the Web server gives an authentication; thus, a mutual communication is enabled. After that, at least a browser image such as an image which is captured by a CCD 221 in the insertion section 204, a motion image according to a method shown at least in FIG. 32, a motion image which is obtained from an image external terminal 235 in the endoscope image device 201 by an image capture I/F 254 in the control section, information (HTML) which relates to the image, an image processing instruction such as a zooming operation for the image, and a switch image (HTML) in which switches are disposed for instructing similar operations to the remote control device 221 are displayed on a display in the external terminal 218. The switch image may be disposed in a similar manner for the switch disposition for the remote control device 212. Also, it is acceptable if a user may customize the disposition freely.

Next, the person who makes decision selects a start for bending the insertion section 204 on the switch image (HTML) which is displayed in the browser so as to monitor the image which is supposed to be observed under condition that the tip section for the insertion section 204 is bent. Such a selection may be performed by using a mice. Alternatively, a touch panel may be disposed so as to be used accordingly. By such a selection, a command HTML script request is completed in a "start bending" in the endoscope control operation. According to this request, the control section 202 establishes a script program so as to convert to a signal for driving the endoscope device 201 and instruct to start bending the insertion section 204 to the endoscope device 201. The endoscope device 201 executes the bending operation for the tip section of the insertion section 204 according to the bending instruction. Also, the control section 202 transmits the HTML which is generated according to the instruction command HTML script request of the bending start to the endoscope to the external terminal so as to update the display in the browser of the control section 202.

Consequently, the endoscope image which is obtained from the CCD 221 successively according to the bending operation is transmitted to the external terminal 218 via the control section 202 and the network; thus, the endoscope image is monitored on the browser display. Such an image is updated successively.

When the endoscope image which includes a desirable observation section is displayed on the browser display, the person who makes decision instructs for recording the image. According to the instruction, the Web browser selects which image record to be stored; thus, the "still image record" command HTML script request is emitted to the control section 202. The control section 202 establishes the script program according to the request so as to convert into the signal for driving the endoscope device 201 and instruct the endoscope device 201 to record the image which is obtained from the CCD 221. Simultaneously, the control section 202 transmits the HTML which is generated according to the record instruction command HTML script request to the endoscope device 201 so as to update the image on the display on the browser in the control section 202. The endoscope device 201 extracts a still image among the motion image which is obtained from the CCD 221 at an instructed timing so as to transmit to the control section 202 by a protocol such as a TCP/IP or a Z-MODE etc. The control section 202 contains the still image in a image database in the RAM 243.

Next, the person who makes decision selects displaying a browsing image which is recorded on the browser display by the external terminal 218. By such a selection, the image browsing HTML script request is transmitted to the control section 202. The control section 202 establishes the script program so as to generate the image browsing HTML. Consequently, the image browsing HTML and its Thumbnail image file are transmitted to the external terminal 218 so as to display the browsing image (thumbnail) on a browser image. If a browsing image (thumbnail) is selected, a still image (JPEG; TIFF) which corresponds to the thumbnail image is displayed.

The person who makes decision can determine the acceptability of the observing section on the sample object which is obtained currently by comparing the sample object which is currently obtained and the image of the former case in the database.

FIG. 34 is a view for a general structure of a endoscope control system according to a seventh embodiment of the present invention. Here, the same reference numerals are added to the members in the second embodiments as those in the above explained sixth embodiment so as to omit the duplication of the explanations.

In the seventh embodiment, explanations are made for a case in which the image (endoscope image), a voice, and a control signal are transmitted/received between the endoscope device 201 and the control section 270 by using a wireless communication or an optical communication. Also, the control section 270 is connected to the network such as a LAN and Internet etc. by a wireless communication such that the external terminal 218 is connected to the network by a wireless communication. In the above explained sixth embodiment, explanations are made for a case in which data in an electric signal format or an optical signal format are transmitted/received by using a cable (electric cable or a optical fiber cable). If a space in which a sample object exists is a narrow space or there is not an inputting terminal for a wired network near there, it is possible to work by using a wireless communication separately from the endoscope device 1; thus, it is possible to realize more comfortable and efficient working condition. By doing this, a wireless communication function and antenna are provided instead of external terminals.

Here, if it is not possible to use a wireless communication, it is acceptable if the data area transmitted/received by connecting via a cable 211. Also, it is acceptable if the image data are transmitted/received by a wired communication and the wireless communication such that either method may be selected appropriately according to the condition in which the sample objects exists. The rest of the structure is similar to that in the above explained sixth embodiment; thus, it is possible to obtain the same operation and effects.

Here, in the above embodiments, it is possible to use an Ethernet, a wireless LAN, a modem, a USB, an IEEE 1394, a BlueTooth, an IEEE 232, an IEEE 422, or an IEEE 485 for the interface which is used for the network communication. Also, a Web server, an image distributing server, a file transmitting server, a mail transmitting and receiving server, or a Telnet server are used for the network communication. Also, more specifically, they are a Web server having an HTTP protocol, a file transmitting server having an FTP (File Transfer Protocol), a mail transmitting server having an SMTP (Simple Mail Transfer Protocol), a mail receiving server having a POP (Post Office Protocol).

As explained above, according to the above embodiments, the main body of the endoscope and other peripheral apparatuses are contained in a case so as to be movable; thus, it is possible to prepare the determination operation quickly. Also, it is possible to exchange the image data (including voice) and a control signal between the endoscope device and the control device by a wireless communication. Therefore, it is possible to observe the sample object even if the sample object is located in a narrow space. Also, if it is not possible to use a wireless communication, it is possible to perform a communication by using a cable connection.

If the observer (a person who performs the examination) cannot determine the acceptability of the sample object, it is possible to observe the sample object so as to determine the acceptability by connecting to the network by using the LAN and Internet easily so as to call up the person who makes decision in a remote place such that the person who makes decision may operate the endoscope device so as to observe the sample object. Also, if a plurality of persons who make decision exist in different remote places, it is possible to observe the same image (endoscope image) simultaneously by using the network communication; thus, it is possible to discuss the observed image so as to make decision more accurately. The determination is made so quickly that it is not necessary to exchange the recording media in which an endoscope image is stored conventionally; thus, it is possible to eliminate a time loss for making decision.

Also, in the network communication, it is not necessary to construct an exclusive network. Instead, only a terminal is necessary. Thus, it is advantageous costwise. Also, a Web server is used; therefore, the user who is connected to the network can use the similar function to those in the control section in the device only by disposing an endoscope control section in the Web server. Thus, it is not necessary to have an exclusive program for each user. It does not consume a capacity for the hard disk in the users external terminal unnecessarily. Also, it is advantageous costwise.

Explanations have been made so far with regards to the above embodiments. In addition, more importantly, the English Specification of the present patent application includes inventions below.

(23) An endoscope system wherein the endoscope device, the endoscope control section, and the terminal are connected by at least a communication section or an image and voice capture section, and the endoscope control section is provided with a server device.

(24) An endoscope system according to the above item (23) wherein the server device distributes endoscope image data of the endoscope device and/or voice data to the terminal.

An endoscope system according to the above item (23) wherein the server section converts an endoscope control request information from the terminal and/or the endoscope control device into control data which can be construed by the endoscope device by using a script.

(26) An endoscope system according to the above item (23) wherein the server section converts an exclusively controllable endoscope control request from the terminal and/or the endoscope control device into control data which can be construed by the endoscope device by using a script.

(27) The control section according to the above item (23) is provided with a display device for displaying the captured image and/or an endoscope image and/or an image of the terminal.

(28) The interface which is used in the above communication device includes an Ethernet, a wireless LAN, a modem, a USB, an IEEE 1394, a BlueTooth, an IEEE 232, an IEEE 422, or an IEEE 485 for the interface which is used for the network communication.

(29) The communication device according to the above item (28) can be switched.

(30) The above image and voice capturing device according to the above item (23) can capture a plurality of images and voices in a switching manner.

(31) The control device according to the above item (23) is provided with a chatting device with a terminal therebetween.

(32) The server device according to the above item (23) is a Web server, an image distributing server, a file transmitting server, a mail transmitting and receiving server, or a Telnet server.

(33) The server according to the above item (32) is a Web server having an HTTP protocol, a file transmitting server having an FTP (File Transfer Protocol), a mail transmitting server having an SMTP (Simple Mail Transfer Protocol), a mail receiving server having a POP (Post Office Protocol).

In the endoscope control system having the above structure, the endoscope device is driven by a remote control operation by a server such as a Web server or a remote control device which uses a network communication so as to determine the acceptability of the sample object which is captured by the endoscope device. Therefore, the information which includes the endoscope image for the sample object is transmitted to the external terminal which can be controlled remotely in the endoscope device via the network so as to perform the determination of the acceptability for the sample object.

Also, in the above endoscope control system which can be controlled remotely, the information which includes the image (endoscope image) of the sample object which is captured by the endoscope device is transmitted to the external terminal which is connected via the network from the control section which has a server so as to be displayed. The driving operation and the controlling operation are performed to the endoscope device by a remote control operation by the external terminal; thus, the sample object is captured; thus, the image is observed. Also, a plurality of external terminals which are disposed in different remote places are connected via the network. Simultaneously, the same image (endoscope image) is transmitted to be displayed. The endoscope device is driven and controlled by a remote control operation by an external terminal to which an authentication is given from the control section; thus, the sample object is captured so as to observe the image.

According to the present invention which is explained above, the endoscope device is controlled remotely by a remote control device which uses the network communication while observing the image which is captured by the endoscope device. Also, the network communication is used such that the endoscope image is provided to a plurality of external terminals which are disposed in remote different places from an observing place. By performing the remote control operation by the external terminals, it is possible to provide an endoscope control system which can capture the endoscope image so as to observe.

Also, according to the present invention, it is possible to provide an endoscope image to a plurality of remotely controllable external terminals from the examination site by using the network communication. Thus, it is possible to provide a remotely controllable endoscope control system by the external terminals.

What is claimed is:

1. An industrial use endoscope control system comprising:
    an endoscope device provided with an insertion section for taking an image of an inner section of a sample object for obtaining an endoscope image;
    a control section connected to the endoscope device via a cable and comprising a server for performing network communication so as to transmit and receive the endoscope image by an electric signal or an optical signal and to control a driving operation for the endoscope device by executing external application software;
    a communication network structure connectable to the control section; and
    at least one external terminal for operating the endoscope device while observing the endoscope image via the communication network,
    wherein the endoscope device is controlled remotely by the external terminal when the external terminal and the control section are connected by the communication network.

2. An The endoscope control system according to claim 1, wherein:
    the control section is provided with a first image and voice capture;
    the at least one external terminal is provided with a server connectable to the communication network structure for operating the endoscope device while observing the endoscope image,
    wherein each external terminal has a second image and voice capture; and
    a mutual communication is performed between the first image with the voice capture and the second image with the voice capture in addition to the endoscope image when the external terminals and the control section are connected via the communication network.

3. The endoscope control system according to claim 2, wherein the server converts an instruction from the external terminal and/or the control section for controlling a driving operation for the endoscope device to a signal for controlling the driving operation for the endoscope device by using a script.

4. The endoscope control system according to claim 1, wherein:
    the remote control device and the external terminal have a microphone and speaker and/or a camera respectively; and
    the remote control device and the external terminal communicate via the communication network such that information regarding conditions at the remote control device and the external terminal are exchanged by voice and image.

5. The endoscope control system according to claim 1, wherein an image display section and an operation switch section are disposed separately in the remote control device, such that the operation switch section is connected to the endoscope device via wireless communication so as to control the driving operation by transmitting an operation signal.

6. The endoscope control system according to claim 1, wherein:
    a connection between the control section and the external terminal is controlled exclusively by an identification number (ID) or a password; and
    the driving operation for the endoscope is controlled only by the external terminal allowed by the control section.

7. The endoscope control system according to claim 1, wherein the external terminal includes a Web browser and a receiving section, the control section including:
    a communication I/F section operable to communicate with the external terminal, the communication I/F section including a transmitting data control section and a received data control section;
    an endoscope control data converting section operable to communicate with the endoscope device, the endoscope control data converting section including a transmitting data control section and a received data control section; and
    a Web server, and
    wherein instruction signals supplied from the external terminal are received by the Web server through the Web browser and the received data control section, the received instruction signals are converted into control signals by the endoscope control data converting section, and the converted signals are transmitted to the endoscope device by the transmitting data control section.

8. An endoscope control system comprising:
    an endoscope device with an insertion section operative to take an image of an inner section of a sample object to obtain an endoscope image so as to transmit the endoscope image via a connection with a communication network;
    a remote control device operative to display the endoscope image, the remote control device operative to connect to the endoscope device via the communication network so as to control the endoscope device remotely while observing the endoscope image outputted from the endoscope device and information related to the outputted image, the remote control device comprising a server operative to receive and execute external application software to control the endoscope device;

at least an external terminal connected to the endoscope via the communication network and configured to operate the endoscope device while observing the endoscope image, wherein the taking the endoscope image by the endoscope device is controlled remotely by the remote control device or the external terminal via the communication network.

9. The endoscope control system according to claim 8, wherein the external terminal includes a Web browser and a receiving section, the control section including:

a communication I/F section operable to communicate with the external terminal, the communication I/F section including a transmitting data control section and a received data control section;

an endoscope control data converting section operable to communicate with the endoscope device, the endoscope control data converting section including a transmitting data control section and a received data control section; and a Web server, and wherein instruction signals supplied from the external terminal are received by the Web server through the Web browser and the received data control section, the received instruction signals are converted into control signals by the endoscope control data converting section, and the converted signals are transmitted to the endoscope device by the transmitting data control section.

10. An endoscope control system comprising:

an endoscope device provided with an insertion section for taking an image of an inner section of a sample object for obtaining an endoscope image;

a control section connected to the endoscope device via wireless communication and comprising a server operative to transmit and receive the endoscope image by an electric signal or an optical signal and to control a driving operation for the endoscope device by executing external application software;

a communication network structure connectable to the control section; and at least an external terminal operative to control the endoscope device while observing the endoscope image via the communication network structure, wherein the endoscope device is controlled remotely by the external terminal when the external terminal and the control section are connected by the communication network structure.

11. The endoscope control system according to claim 10, wherein the external terminal includes a Web browser and a receiving section, the control section including:

a communication I/F section operable to communicate with the external terminal, the communication I/F section including a transmitting data control section and a received data control section;

an endoscope control data converting section operable to communicate with the endoscope device, the endoscope control data converting section including a transmitting data control section and a received data control section; and a Web server, and wherein instruction signals supplied from the external terminal are received by the Web server through the Web browser and the received data control section, the received instruction signals are converted into control signals by the endoscope control data converting section, and the converted signals are transmitted to the endoscope device by the transmitting data control section.

* * * * *